(12) United States Patent
Mosesov et al.

(10) Patent No.: US 11,612,334 B2
(45) Date of Patent: Mar. 28, 2023

(54) METHODS OF ASSESSING CONTACT BETWEEN AN ELECTRODE AND TISSUE USING COMPLEX IMPEDANCE MEASUREMENTS

(71) Applicant: St. Jude Medical, Cardiology Division, Inc., St. Paul, MN (US)

(72) Inventors: Artem Mosesov, Roseville, MN (US); Timothy G. Curran, St. Paul, MN (US)

(73) Assignee: ST. JUDE MEDICAL, CARDIOLOGY DIVISION, INC., St. Paul, MN (US)

(*) Notice: Subject to any disclaimer, the term of this patent is extended or adjusted under 35 U.S.C. 154(b) by 1134 days.

(21) Appl. No.: 16/225,154

(22) Filed: Dec. 19, 2018

(65) Prior Publication Data
US 2019/0183378 A1 Jun. 20, 2019

Related U.S. Application Data

(60) Provisional application No. 62/607,554, filed on Dec. 19, 2017.

(51) Int. Cl.
*A61B 5/0538* (2021.01)
*A61B 18/14* (2006.01)
(Continued)

(52) U.S. Cl.
CPC ............ *A61B 5/0538* (2013.01); *A61B 5/068* (2013.01); *A61B 5/283* (2021.01); *A61B 5/6846* (2013.01);
(Continued)

(58) Field of Classification Search
CPC ....... A61B 5/0538; A61B 5/068; A61B 5/283; A61B 5/6846; A61B 5/6852;
(Continued)

(56) References Cited

U.S. PATENT DOCUMENTS

| 4,587,975 A | 5/1986 | Salo |
| 5,341,807 A | 8/1994 | Nardella |

(Continued)

FOREIGN PATENT DOCUMENTS

| CN | 101534736 | 9/2009 |
| CN | 102355856 | 2/2012 |

(Continued)

OTHER PUBLICATIONS

Assambo, C., "Determination of the Parameters of the Skin-Electrode Impedance Model for ECG Measurement," Proceedings of the 6th WSEAS Int. Conf. On Electronics, Hardware, Wireless and Optical Communications, pp. 90-95, Feb. 2007.

(Continued)

*Primary Examiner* — Jung Kim
(74) *Attorney, Agent, or Firm* — Billion & Armitage

(57) ABSTRACT

A system and method measures impedance across a plurality of electrodes and assesses proximity or contact between electrodes of a medical device and patient tissue. Contact is assessed between individual electrodes and cardiac tissue using bipolar electrode complex impedance measurements. Initially, baseline impedance values are established for each of the individual electrodes based on the responses of the electrodes to the applied drive signals. After establishing the baseline impedance values a series of subsequent impedance values are measured for each electrode. For each electrode, each subsequent impedance value may be compared to a previous baseline impedance value for that electrode. If a subsequent impedance value is less than the baseline impedance value for a given electrode, the baseline impedance value may be reset to the subsequent impedance value. Such systems and method are particularly applicable to medical devices having numerous electrodes.

20 Claims, 24 Drawing Sheets

(51) Int. Cl.
*A61B 5/06* (2006.01)
*A61B 18/12* (2006.01)
*A61B 5/00* (2006.01)
*A61B 5/283* (2021.01)
*A61B 18/00* (2006.01)

(52) U.S. Cl.
CPC .......... *A61B 5/6852* (2013.01); *A61B 5/6869* (2013.01); *A61B 5/7225* (2013.01); *A61B 18/1206* (2013.01); *A61B 18/1492* (2013.01); *A61B 2018/00577* (2013.01); *A61B 2018/00648* (2013.01); *A61B 2018/00875* (2013.01); *A61B 2018/126* (2013.01); *A61B 2018/1253* (2013.01)

(58) Field of Classification Search
CPC ................ A61B 5/6869; A61B 5/7225; A61B 18/1206; A61B 18/1492; A61B 2018/00577; A61B 2018/00648; A61B 2018/00875; A61B 2018/1253; A61B 2018/126
See application file for complete search history.

(56) References Cited

U.S. PATENT DOCUMENTS

| | | | |
|---|---|---|---|
| 5,469,857 A | 11/1995 | Laurent et al. | |
| 5,836,990 A | 11/1998 | Li | |
| 6,129,669 A | 10/2000 | Panescu et al. | |
| 6,391,024 B1 | 5/2002 | Sun et al. | |
| 6,471,693 B1 | 10/2002 | Carroll et al. | |
| 6,546,270 B1 | 4/2003 | Goldin et al. | |
| 6,569,160 B1 | 5/2003 | Goldin et al. | |
| 7,263,397 B2 | 8/2007 | Hauck et al. | |
| 8,160,690 B2 | 4/2012 | Wilfley et al. | |
| 8,369,922 B2 | 2/2013 | Paul et al. | |
| 8,403,925 B2 | 3/2013 | Miller et al. | |
| 8,406,866 B2 | 3/2013 | Deno et al. | |
| 8,672,936 B2 | 3/2014 | Thao et al. | |
| 9,687,289 B2 | 6/2017 | Govari et al. | |
| 9,750,570 B2 | 9/2017 | Condie et al. | |
| 2004/0230131 A1 | 11/2004 | Kassab et al. | |
| 2007/0060833 A1 | 3/2007 | Hauck | |
| 2007/0123764 A1 | 5/2007 | Thao et al. | |
| 2008/0275442 A1 | 11/2008 | Saurav et al. | |
| 2008/0312713 A1 | 12/2008 | Wilfley et al. | |
| 2009/0158852 A1 | 6/2009 | Saurav et al. | |
| 2010/0010612 A1 | 1/2010 | Gelbart et al. | |
| 2010/0168560 A1 | 7/2010 | Hauck et al. | |
| 2010/0217132 A1 | 8/2010 | Ellingwood et al. | |
| 2011/0306867 A1 | 12/2011 | Gopinathan et al. | |
| 2012/0078342 A1 | 3/2012 | Volkron et al. | |
| 2012/0172702 A1 | 7/2012 | Koyrakh et al. | |
| 2012/0203169 A1 | 8/2012 | Tegg | |
| 2012/0238897 A1 | 9/2012 | Wilfley et al. | |
| 2013/0324993 A1 | 12/2013 | McCarthy et al. | |
| 2014/0364715 A1 | 12/2014 | Hauck | |
| 2016/0242667 A1 | 8/2016 | Fay et al. | |
| 2016/0287136 A1 | 10/2016 | Condie et al. | |
| 2019/0282292 A1* | 9/2019 | Wiener .............. | A61B 18/1233 |

FOREIGN PATENT DOCUMENTS

| | | |
|---|---|---|
| EP | 1169976 | 1/2002 |
| EP | 1962945 B1 | 4/2016 |
| JP | 2010514504 A | 5/2010 |
| JP | 2014529419 A | 11/2014 |
| JP | 2016502885 A | 2/2016 |
| WO | 2000078239 | 12/2000 |
| WO | 2010020958 | 2/2010 |
| WO | 2011060497 A1 | 5/2011 |
| WO | 2013162884 A1 | 10/2013 |
| WO | 2016081650 A1 | 5/2016 |
| WO | 2016081786 A1 | 5/2016 |
| WO | 2016181315 A1 | 11/2016 |
| WO | 2017160808 A1 | 9/2017 |

OTHER PUBLICATIONS

International Search Report for International Application No. PCT/US2018/066384, dated Apr. 11, 2019.

* cited by examiner

METHODS OF ASSESSING CONTACT BETWEEN AN ELECTRODE AND TISSUE USING COMPLEX IMPEDANCE MEASUREMENTS

CROSS REFERENCE

The present application claims the benefit of the filing date of U.S. Provisional Application No. 62/607,554 having a filing date of Dec. 19, 2017, the entire contents of which is incorporated herein by reference.

BACKGROUND a. Technical Field

The instant disclosure relates to electrical impedance-based measurement of electrodes of a medical device to determine, among other things, contact between tissue and the electrodes of the medical device. More specifically, the disclosure relates to simultaneously sensing the proximity of multiple electrodes to tissue in a body b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site such as, for example, a site within the patient's heart. The catheter typically carries one or more electrodes, which may be used for ablation, diagnosis, and the like.

In many procedures, it may be beneficial to know the contact status of an electrode (e.g., in contact with tissue, in a blood pool) on a catheter. For example, in an electrophysiology mapping procedure, the electrical signal present on an electrode may vary depending on whether the electrode is in contact with tissue, or adjacent to the tissue in a blood pool, and that difference may be accounted for in software. In another example, in an ablation procedure, it may be desirable to only drive an ablation current when an electrode is in contact with the tissue to be ablated.

One existing methodology that may be used to determine whether an electrode on a catheter is in contact with tissue includes driving a current between the electrode and an electrode elsewhere within the patient (e.g., at a stable position within the patient) or on the exterior of the patient (e.g., on the patient's skin) and assessing the impedance between the electrodes. To determine an impedance between those electrodes, the electric potential of the electrode on the medical device may be referenced to a third electrode, which may also be elsewhere within the patient or on the exterior of the patient.

The foregoing discussion is intended only to illustrate the present field and should not be taken as a disavowal of claim scope.

BRIEF SUMMARY

Measuring the impedance of an electrode has been demonstrated to provide a reliable method of detecting when an electrode comes in contact with tissue (e.g., intracardiac tissue). Specifically, due to the reduced conductivity of tissue compared to blood, the impedance of an electrode is significantly higher once it comes in contact with the tissue than when the electrode is disposed within a blood pool (e.g., internal patient cavity). The present disclosure is directed to assessing contact between an electrode and tissue using impedance measurements. In one embodiment, the disclosure is directed to assessing contact between an electrode and cardiac tissue using bipolar electrode complex impedance measurements. Such assessment may be implemented in a system, such as an electronic control unit, which measures impedances between electrodes of a connected medical device. Such a system may include a controller or frequency source configured to generate a plurality of drive signals. Each of the drive signals may have a unique modulation frequency that may be a harmonic of a common base frequency. The controller or frequency source may further be configured to simultaneously apply each of the plurality of drive signals across an individual pair of electrodes of the connected medical device. The medical device may be a catheter. However, the system is not limited to use with catheters and may be utilized with other medical devices. The system may include a measurement circuit for measuring responses of the drive signals as applied to individual pairs of electrodes of the medical device. The measurement circuit may include a demodulator that is configured to simultaneously demodulate the response signal(s) for each unique drive frequency. The demodulator may generate demodulation signals each having an identical frequency to one unique frequency of the drive signal and known phase that is different than a phase of the unique frequency. Such demodulation may include quadrature demodulation to provide in-phase and quadrature channels. Additional hardware and/or software may scale the results to resistive and reactive impedance in units of ohms.

In one arrangement, a system and method are provided for establishing baseline impedance values for electrodes of a medical device such that subsequent impedance changes of those electrodes may be utilized to assess tissue contact and/or when an electrode enters and exits an introducer (i.e., is sheathed or unsheathed). The system and method include simultaneously applying a plurality of drive signals having unique frequencies across different individual pairs of electrodes of a medical device. Initially, a baseline impedance value is measured for each of the plurality of electrodes based on the responses of the electrodes to the applied drive signals. Measuring the impedance values may further include synchronously demodulating responses of the electrodes to the simultaneously applied drive signals. The application of the drive signals and measuring of impedance values may continue over a predetermined period of time. Accordingly, after the initial impedance measurements, a series of subsequent impedance values may be measured for each electrode. For each electrode, each subsequent impedance value may be compared to a previous baseline impedance value for that electrode. If a subsequent impedance value is less than the baseline impedance value for a given electrode, the baseline impedance value may be reset to the subsequent impedance value. In this regard, the lowest measured impedance value may be established as a baseline impedance value for a given electrode.

The system and method may each be utilized for medical devices having a high number of electrodes. In such applications, a medical device may be moved relative to an internal patient cavity in conjunction with measuring the impedance values. Such movement allows the electrodes to move into and out of contact with patient tissue. The near continuous measurement of impedance values in conjunction with the movement of the medical device allows for determining baseline impedance values while the electrodes of the medical device are free of contact with patient tissue.

The system and method may further include comparing subsequent impedance values to an establish baseline impedance values to generate an indication of tissue proximity between an electrode and patient tissue. For example, if a subsequent impedance value is greater than a baseline impedance value, the change between the subsequent impedance value and the baseline impedance value may be assessed to determine tissue proximity. Such an indication of tissue proximity may include a binary indication of contact and noncontact between an electrode and tissue. Alternatively, the indication of tissue proximity may provide a range of contact conditions between the electrode and the tissue. Further, the established baseline impedance values may be utilized to determine when an electrode is sheathed or unsheathed.

The system and method may further include displaying indications of tissue proximity for each electrode on a display device. In addition, such displaying may include identifying a location of each electrode relative to an internal patient cavity such that the indication of tissue proximity may be displayed at a corresponding location of a map of the internal patient cavity.

In another arrangement, a system and method are provided for dynamically establishing baseline impedance values for electrodes of a medical device during a medical procedure and generating an indication of tissue proximity between the electrodes and patient tissue. The system and method include applying a plurality of drive signals, each having a unique frequency, across different individual pairs of electrodes of a medical device. The drive signals may be applied in conjunction with the application of, for example, ablation energy to one or more of the electrodes. A series of impedance values may be measured for each of the plurality of electrodes in response the applied drive signals. Each of the series of impedance values may be compared to a prior baseline impedance value for the electrode. If the subsequent impedance value is greater than the baseline impedance value, an indication of tissue proximity may be generated and displayed on a display device. This may entail identifying a location of the electrode relative to an internal patient cavity, wherein the indication of tissue proximity is displayed on the display device at a corresponding location of a map of the internal patient cavity. If a subsequent impedance value is lower than the baseline impedance value, the baseline impedance value may be reset to the subsequent impedance value.

In either of the noted systems or methods, the impedance values may comprise complex impedance values having an in-phase (e.g., real) component and a quadrature (e.g., imaginary) component. In one arrangement, generating an indication of tissue proximity may be based on one of the components of the complex impedance value. In one specific arrangement, the real component of an impedance value may be compared to a real component of a baseline impedance value to provide an indication of tissue contact. In this arrangement, the quadrature components of the impedance values may be compared to determine interference resulting from, for example, contact and/or proximity to structures other than tissue. By way of example, the quadrature components of the impedance values may be used to identify when an electrode is sheathed or unsheathed and/or when an electrode contacts another electrode.

In either of the noted systems or methods, subsequent impedance values may be utilized to generate an indication of a change in patient tissue. By way of example, a change between a subsequent impedance value and a baseline impedance value may provide an indication of lesion formation in patient tissue during an ablation procedure.

In a further arrangement, a system and method are provided for determining spatially dependent baseline impedance values. In this arrangement, baseline impedance values are determined for specific locations within, for example, a three-dimensional space such as an internal patient cavity. Subsequent changes of impedance values are assessed on a location-by-location basis rather than being assessed on an electrode-by-electrode basis. The method includes identifying a location of each electrode of a medical device in the three-dimensional space. That is, each electrode may be identified within a sub-region of the three-dimensional space. The sub-regions may be defined as a grid or other sub-division of the three-dimensional space. Drive signals are applied to each of the electrodes of the medical device and responses of the electrodes to the drive signals are measured. Impedance values are generated for each electrode. Based on location of the electrode in the three-dimensional space and the impedance value for that electrode, sub-regions of the three-dimensional space are assigned baseline impedance values. That is, a sub-region containing an electrode is assigned the impedance value for that electrode as a baseline impedance value. Subsequent impedance values for an electrode located in the sub-region are compared to the baseline impedance value for that sub-region. If the subsequent impedance value for a sub-region is greater than the baseline impedance value for the sub-region, an indication of tissue proximity between the electrode and tissue may be generated. If the subsequent impedance value for the sub-region is less than the baseline impedance value for the sub-region, the baseline impedance value may be reset to the subsequent impedance value. The system and method may further include moving electrodes of the medical device throughout the three-dimensional space to assign baseline impedance values to most or all sub-regions of the three-dimensional space. The method may also be used to generate indications of lesion formation in each sub-region during, for example, an ablation procedure.

DETAILED DESCRIPTION

Figure 1:
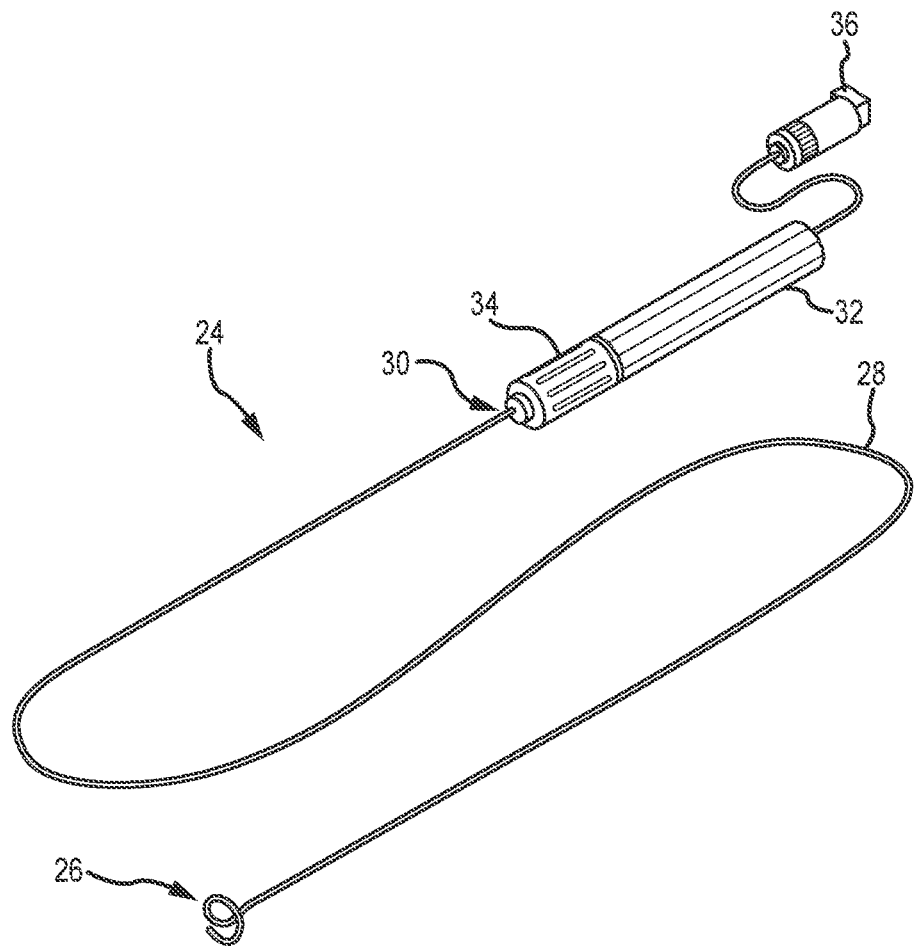
FIG. 1 is an isometric view of an exemplary embodiment of an elongate medical device having a distal lariat portion.

Referring now to the figures, in which like numerals indicate the same or similar elements in the various views, FIG. 1 is an isometric view of an exemplary embodiment of an elongate medical device 24. The elongate medical device 24 may comprise, for example, a diagnostic and/or therapy delivery catheter, an introducer or sheath, or other like devices. For purposes of illustration and clarity, the description below will be with respect to an embodiment where the elongate medical device 24 comprises a catheter (i.e., catheter 24). It will be appreciated, however, that embodiments wherein the elongate medical device 24 comprises an elongate medical device other than a catheter remain within the spirit and scope of the present disclosure.

Referring to FIG. 1, the catheter 24 may comprise a shaft 28 having a distal end portion 26 and a proximal end portion 30. The catheter 24 may be configured to be guided through and disposed in the body of a patient. Accordingly, the proximal end portion 30 of the shaft 28 may be coupled to a handle 32, which may include features to enable a physician to guide the distal end portion to perform a diagnostic or therapeutic procedure such as, for example only, an ablation or mapping procedure on the heart of the patient. Accordingly, the handle 32 may include one or more manual manipulation mechanisms 34 such as, for example, rotational mechanisms and/or longitudinal mechanisms, coupled to pull wires for deflecting the distal end portion of the shaft. Exemplary embodiments of manipulation mechanisms, pull wires, and related hardware are described, for example only, in U.S. patent application publication no. 2012/0203169, hereby incorporated by reference in its entirety. The handle 32 may further include one or more electromechanical connectors for coupling to a mapping and navigation system, an ablation generator, and/or other external systems. The handle 32 may also include one or more fluid connectors 36 for coupling to a source and/or destination of fluids such as, for example only, a gravity feed or fixed or variable-rate pump. Accordingly, the distal end portion 26 of the shaft 28 may also include one or more fluid ports or manifolds for distributing or collecting fluids such as, for example only, irrigation fluid during an ablation procedure. The fluid ports may be fluidly coupled with one or more fluid lumens extending through the shaft 28 to the handle 32. In some embodiments, the elongate medical device 24 may comprise an introducer that includes at least one lumen configured to receive another device such as a catheter or probe.

Figure 2:
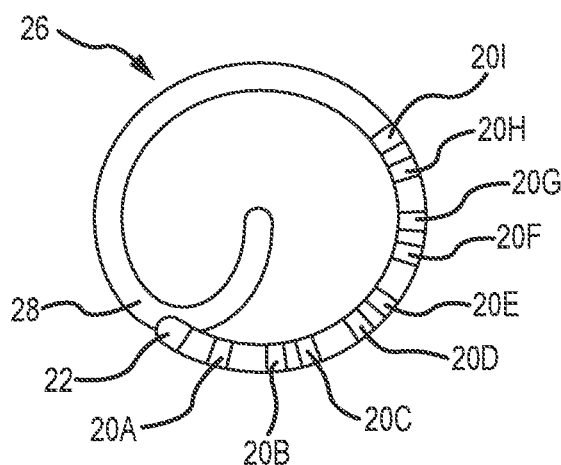
FIG. 2 is an end view of the distal end portion of the elongate medical device of FIG. 2, illustrating multiple electrodes that may be used on the device.

The distal end portion 26 of the shaft 28 of the exemplary catheter 24 may have a lariat shape. See also FIG. 2. In this embodiment, the lariat shape may be formed by, for example, a shape memory wire disposed within the shaft. A tip electrode 22 and a number of ring electrodes 20A, 20B, 20C, 20D, 20E, 20F, 20G, 20H, 20I (which, may be referred to herein individually and generically as a ring electrode 20 or in the multiple as the ring electrodes 20) may be disposed on the distal end portion 26 of the shaft 28. For example, the tip electrode 22 and ring electrodes 20 may be disposed on the lariat portion of the shaft 28. In the illustrated embodiment, the distal end portion 26 includes nine (9) ring electrodes 20 (i.e., a "decapolar" catheter having ten total electrodes, as illustrated in FIG. 2). In other embodiments, the distal end portion 26 includes nineteen (19) ring electrodes 20 (i.e., a "duo-decapolar" catheter having twenty total electrodes). The electrodes 20, 22 on the catheter 24 illustrated in FIGS. 1 and 2 may be used for applying ablation energy to tissue, acquiring electrophysiology data from tissue, determining the position and orientation (P&O) of the shaft, and/or other purposes. The electrodes 20, 22 may be coupled to electrical wiring within the shaft 28, which may extend to the handle 32 and to electromechanical connectors for coupling to external systems. The ring electrodes 20 may be placed in pairs, in one non-limiting embodiment, with two electrodes 20 in a pair disposed a first distance away from each other along the length of the shaft 28, and second pair of electrodes 20 separated by a second distance along the length of the shaft 28. For example, electrodes 20B and 20C (e.g., bi-pole pair of electrodes) may be considered a first pair, electrodes 20D and 20E may be considered a second pair, and so on. These distances may be equal, or the first distance may be different than the second distance. It will be appreciated that the catheter, 24 illustrated in FIGS. 1 and 2 is exemplary in nature only. The teachings of the present disclosure may find use with numerous other medical devices, such as circular mapping catheters, other known mapping and diagnostic catheters, and other known medical devices.

An elongate medical device having multiple electrodes, such as the catheter 24, may find use in a system for assessing a state of contact between the elongate medical device and the tissue of a patient. As mentioned in the Background, in some known systems, an electrical current may be driven between an electrode on an elongate medical device disposed within the body and a cutaneous electrode to assess such contact. The electric potential on the in-body electrode may be measured with reference to a third electrode (e.g., another cutaneous electrode), and an impedance may be calculated, where such an impedance may indicate a contact state. Such a uni-polar system and methodology may be improved upon by a system for assessing a contact state according to an electrical current driven between two electrodes on the same device (e.g., on the same elongate medical device within the patient's body). That is, impedance may be measured between a pair of electrodes (e.g., bi-pole pair of electrodes), on the same device, eliminating artifacts that may appear in a uni-polar arrangement. For instance, in a uni-polar arrangement some of the current between the internal electrode and the external electrode must pass through the lungs of a patient, which changes impedance with each breath.

Figure 3:
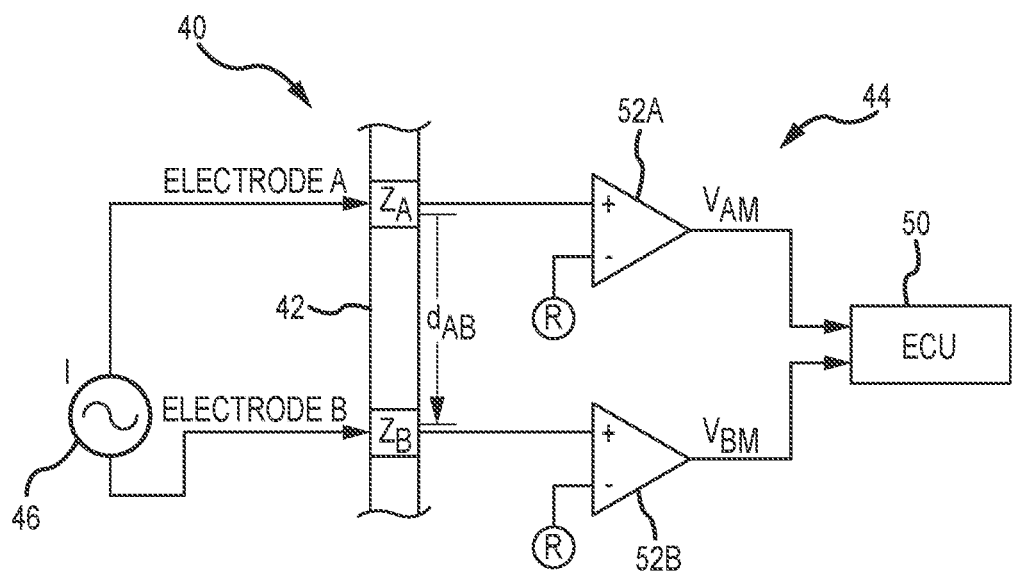
FIG. 3 is a diagrammatic view of an exemplary embodiment of a system for determining an impedance at two electrodes on an elongate medical device.

FIG. 3 is a diagrammatic view of a system 40 for assessing a contact state according to an electrical current driven between two electrodes (e.g., a bi-pole electrode) on the same device. The system 40 may include a medical device 42 comprising at least two electrodes A, B having respective impedances $Z_A$, $Z_B$, a detection amplifier 44, and a signal generator 46. The detection amplifier may include, in one non-limiting embodiment, two operational amplifiers (op amps) $52_A$, $52_B$, a reference electrode R, and a measurement circuit or impedance sensor, which may be part of an electronic control unit (ECU) 50. In one embodiment, the signal generator may be incorporated in or may be considered a part of the ECU.

The medical device 42 may be or may include an elongate medical device such as the catheter 24 (see FIG. 1). The electrodes A, B may be any two electrodes on the device. For example, referring to FIG. 2, the electrodes A, B may be the tip electrode 22 and the first ring electrode 22A. Alternatively, the electrodes A, B may be two ring electrodes 20D and 20E, or 20F and 20G, etc.

The signal generator 46 may be configured to generate (e.g., among other signals), a drive signal or excitation signal across the electrodes A, B (i.e., using one electrode as a source and the other as a sink). In one embodiment, the drive signal may have a frequency within a range from about 1 kHz to over 500 kHz, more typically within a range of about 2 kHz to 200 kHz, and even more typically about 20 kHz. In one embodiment, the drive signal may be a constant current signal, typically in the range of between 20-200 μA, and more typically about 100 μA.

The ECU 50 may include conventional filters (e.g., bandpass filters) to block frequencies that are not of interest, but permit appropriate frequencies, such as the drive frequency, to pass, as well as conventional signal processing software used to obtain the component parts of the measured complex impedance. Accordingly, the ECU 50 may include a memory storing such signal processing software and a processor configured to execute the signal processing software. The ECU 50 may include any processing apparatus such as, as noted above, a memory and a processor. Additionally, or alternatively, the impedance sensor may include an application-specific integrated circuit (ASIC), programmable logic device (PLD), field-programmable gate array (FPGA), and/or other processing device.

The detection amplifier 44 may have a positive polarity connector (e.g., first channel) which may be electrically connected to a first electrode A and a negative polarity connector (e.g., second channel) which may be electrically connected to a second electrode B. The positive and negative polarity connectors may be disposed relative to the other components of the detection amplifier 44 so as to form the circuit diagrammatically shown in FIG. 3 when connected with the electrodes A, B. It should be understood that the term connectors as used herein does not imply a particular type of physical interface mechanism but is rather broadly contemplated to represent one or more electrical nodes.

The detection amplifier may drive a current between electrodes A, B on the same device to assess a contact state between the electrodes A, B and tissue. Impedances may be calculated based on those driven currents to determine a contact state. The system may be configured to determine impedances respective of the first and second electrodes A, B to determine a contact state.

Determination of impedances may begin with driving a sinusoidal electrical signal (e.g., drive signal or excitation signal) between electrodes A and B, with one of electrodes A and B selected as a source, and the other as a sink. The source and sink selection may be made by the ECU 50, and the current driven by the signal generator 46. The drive signal may have predetermined characteristics (e.g., frequency and amplitude). Electrical potentials are measured on electrodes A and B while driving the current between electrodes A and B. The potentials may be measured by a detection amplifier, in an embodiment. The detection amplifier may present a very high impedance (for example, about 100 kΩ or more, in an embodiment, and/or 50 times or more greater than the nominal impedance of one of the electrodes A, B, in an embodiment, and/or 100 times or more greater than the nominal impedance of one of the electrodes A, B, in an embodiment) relative to the path between electrodes A and B, so the effect of measurements with the detection amplifier on the potential on the electrodes A, B may be negligible.

Measurement may further include referencing the measured electric potentials to a reference electrode, such as electrode R (shown in FIG. 3). Reference electrode R may be a cutaneous electrode, such as a body patch electrode, in an embodiment. Alternatively, the reference electrode R may be another in-patient electrode. Such referencing may be performed by inputting the potential on electrode A into a first input of the first op amp $52_A$, the potential on electrode B into a first input of the second op amp $52_B$, and the potential on the reference electrode into respective second inputs on both the first op amp $52_A$ and the second op amp $52_B$. The output of the op amps $52_A$, $52_B$ may be input to the ECU 50 for impedance determinations, contact assessment, and/or other calculations. In another embodiment, hardware separate from the ECU 50 may be provided to perform some or all of the impedance and/or contact determinations.

For driving the current between electrodes A and B and determining electric potentials on electrodes A and B, known methods of driving a current at a particular carrier frequency and demodulating the respective potentials on electrodes A and B may be used. The detection amplifier may amplify the signals manifest on each electrode A, B, and after demodulation a voltage related to the impedance of each electrode is available. In the case of electrode B, the recovered voltage will be negative (i.e., assuming electrode A is selected as the source and B as the sink), so a conversion to a positive quantity may be applied by the ECU 50 or other device. Since the current source-sink electrode pair may comprise a closely spaced bi-pole, the potential at the reference electrode R with respect to the bi-pole will be similar, and thus the physical location of R may vary with little effect on the voltages between A and R and B and R.

For a given electrode geometry for which impedance is measured at a sufficiently high frequency, the potential measured for a current driven between electrodes A, B may be essentially resistive in a pure saline or blood medium, and may reflect the electrode's geometry and the solution conductivity. For example, a spherical electrode in a homogenous medium will have an electric potential for a current driven through the electrode according to equation (1) below:

$$V = \frac{\rho I}{4\pi r} \qquad (1)$$

where V is the electric potential, I is the applied current, p is the media resistivity, and r is the distance from the center of the electrode at which the potential measurement is made. The measured impedance may be taken as the measured potential on the electrode divided by the applied current, as set forth in equation (2) below:

$$Z = \frac{V}{I} \qquad (2)$$

Calculation of impedance based on electrode geometry is well known. Along these lines, equations for ring electrodes and/or conversions from a spherical electrode to a ring electrode are known. Further, the effect of the influence of one electrode (e.g., A) on another electrode (e.g., B) of and electrode pair can be calculated and accounted for. Exemplary embodiments for calculating impedance based on electrode geometry and accounting for effects of influence of an adjacent electrode are described, for example only, in U.S. patent application publication no. 2014/0364715, hereby incorporated by reference in its entirety.

For each potential measured as a current is driven between electrodes A and B, geometry specific equations may be solved (e.g., by the ECU 12) to determine the voltages on each of electrodes A and B (relative to reference electrode R). Accordingly, such equations may be stored in the memory of the ECU 50 for execution by the processor of the ECU 50. Those voltages may then be applied to equation (1) or another geometric specific equation to determine impedances respective of each of electrode A and B (again, by the ECU 50, for example). Based on those impedances, a contact state between electrodes A and B and the tissue of a patient may be assessed. Such measurements may be carried out numerous times. Furthermore, such measurements may be carried out for numerous sets of electrodes A and B. That is, impedance potentials may be carried out repeatedly for numerous different pairs of electrodes to determine a contact state for each of those electrodes. For example, referring to FIGS. 1 and 2, the measurements may first be carried out on electrodes 22 and 20A, then on 20B and 20C, then on 20D and 20E, and so on. Stated otherwise, the impedance of pairs of electrodes may be determined sequentially.

Figure 4:
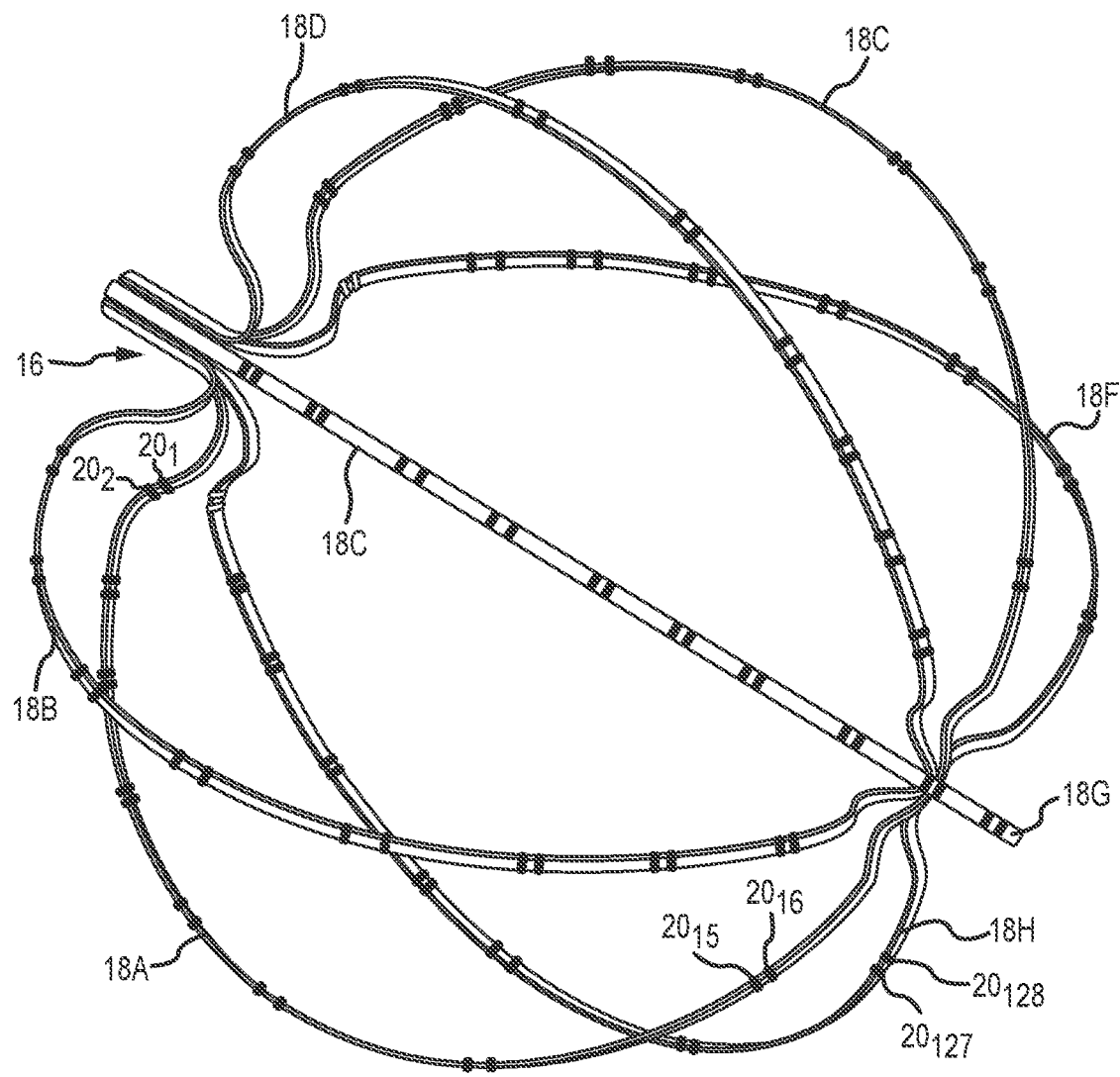
FIG. 4 is an end view of a distal end portion of an alternate embodiment of an elongate medical device illustrating a high electrode count.

While contact assessments based on a current driven between electrode pairs on a catheter (or other medical device) provides increased accuracy in comparison to contact assessments based on a current driven between an electrode on a catheter and an exterior/cutaneous electrode, aspects of the present disclosure are based, in part, on the realization that previous contact assessment systems have limitations. One specific limitation is that medical standards establish current limits (auxiliary current) for medical devices. For instance, such industry standards allow for 10 micro-amps of current for an intra-cardiac electrode for AC currents below 1 kHz. At 10 kHz, the limit is 100 micro-amps with proportionally increasing limits with increasing frequency (i.e., at 20 kHz the limit is 200 micro-amps). The auxiliary current limitation (e.g., threshold) works against a current trend in electrode catheters. Namely, the increasing number of electrodes carried on a catheter (or other medical device) to improve, for example, mapping accuracy and/or ablation control. By way of example, one existing electrode catheter, the FIRMmap basket catheter by Topera/Abbott Laboratories, utilizes 64 separate electrodes. Other proposed catheters contain 100 or even 200 separate electrodes. FIG. 4 illustrates a distal end of an exemplary catheter 16 having 128 electrodes. $20_1$-$20_{128}$. In the illustrated embodiment, the distal end of the catheter 16 is formed as an expandable basket having eight arms 18a-h. The arms 18a-h may be formed from shape metal wires such that they expand to the illustrated shape when disposed through the end of, for example, an introducer. Each arm includes 16 electrodes forming eight pairs of electrodes. In the case of such a 128-electrode catheter, impedance of 64 electrode pairs may be sequentially determined. Such sequential determination of such a large number of electrode pairs reduces the response time of the system. Another solution is to simultaneously drive current across each pair of electrodes. However, if the electrodes pair are driven with a current at a common or single frequency, cross talk between the electrode pairs makes identifying the response of any given pair of electrodes difficult or impossible. Additionally, driving a current across a plurality of electrode pairs at a single frequency results in additive auxiliary current (e.g., at a surface electrode or other internal electrode). For instance, for an auxiliary current limit of 100 micro-amps (e.g., excitation frequency at 10 kHz), a catheter having 40 electrodes (i.e., 20 bi-poles or pairs of electrodes) would be limited to using a 5 micro-amp current (i.e., 20 bi-poles*5 micro-amps=100 micro-amps). The sum current is an additive total of all of the channel pairs. For a catheter having 100 pairs of electrodes (e.g., bi-poles), the drive current would be limited to 1.0 micro-amps. As the number of electrodes increases, the magnitude of the drive current must decrease to maintain the sum current below threshold auxiliary current limits. As will be appreciated, lowering the magnitude of the drive current applied across each bi-pole reduces the signal-to-noise ratio of its response. Accordingly, for medical devices with high numbers of electrodes, the response of the bi-pole pairs of electrodes may be overwhelmed by noise.

Aspects of the present disclosure are further based on the recognition that utilization of multiple drive signals having multiple different frequencies (e.g., unique frequencies) allows for increasing the magnitude of the drive current for each pair of electrodes (e.g., bi-pole) or increasing the number of bi-poles without exceeding auxiliary current limits/thresholds. That is, it has been recognized that the sum current where multiple bi-poles are excited by multiple drive signals each having different/unique frequencies rises with the square root of the number of channels. In such a configuration, the total measured current or sum current is:

$$Itotal = Ifrequency * \sqrt{Nfrequencies} = Ifrequency * \sqrt{\left(\frac{Nchannels2}{\Box}\right)} \qquad (3)$$

Where Ifrequency is the current per frequency (i.e., per bi-pole electrode pair) and Nfrequencies is the total number of frequencies. Note the total number of channels is twice the number of frequencies (since one frequency services a bi-pole electrode pair). For example, for a medical device or catheter having 200 electrodes, 100 different frequencies would be used. Assuming these frequencies are above 10 kHz (e.g., spaced every 25 Hz over a 2500 Hz band 15-17.5 kHz), drive signals having a 5 micro-amp current would result in a sum current of no more than 50 micro-amps (i.e., 5 micro-amps*√100), well below the 100 micro-amp limit for 10 kHz. Of note, the actual safe current limit is greater than 100 micro-amps as each additional frequency is higher than the previous frequency and thus greater than 10 kHz. However, the 100 micro-amp limit is utilized for simplicity.

Figure 5:
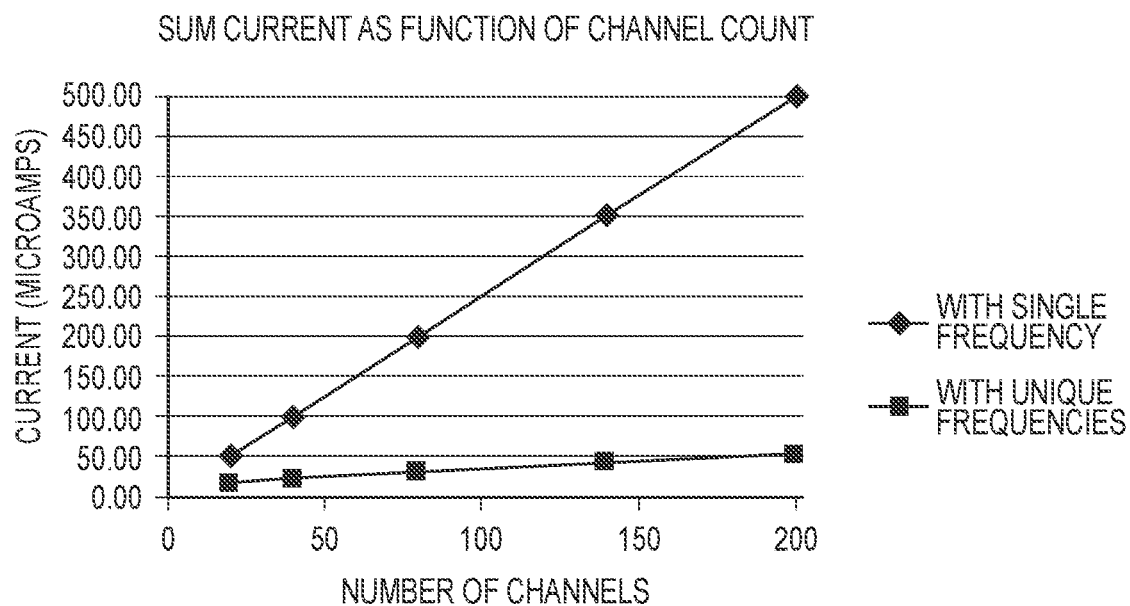
FIG. 5 is a chart illustrating a sum current as a function of channel count.

The reduction of the sum current resulting from use of multiple unique frequencies compared to the single frequency example discussed above (i.e., 100 bi-poles; 1 micro-amp drive current; 100 micro-amp sum current) occurs in conjunction with a five-fold increase in the magnitude of the drive current (i.e., 5 micro-amps vs. 1 micro-amp). This is illustrated in the chart of FIG. 5. As the chart demonstrates, the application of a single frequency drive signal with a 5 micro-amp drive current, 100 micro-amps is reached at 40 channels (e.g., 20 bi-pole at 5 micro-amps each) while only 50 micro-amps is reached at 200 channels when using unique frequencies. The use of unique frequencies provides a significant advantage in increasing the total number of electrode for a medical device.

Equation (3) may be rearranged to find the maximum number of channels for a given drive current:

$$N channels = 2\left(\frac{Itotal}{Ifrequency}\right)^2 \quad (4)$$

Thus, with 5 micro-amps per bi-pole at 10 kHz and higher (using a flat 100 micro-amp auxiliary limit/threshold for simplicity) the maximum number of channels is:

$$2\left(\frac{100\ uA}{5\ uA}\right)^2 = 2(20^2) = 800\ \text{channels} \quad (5)$$

Figure 6:
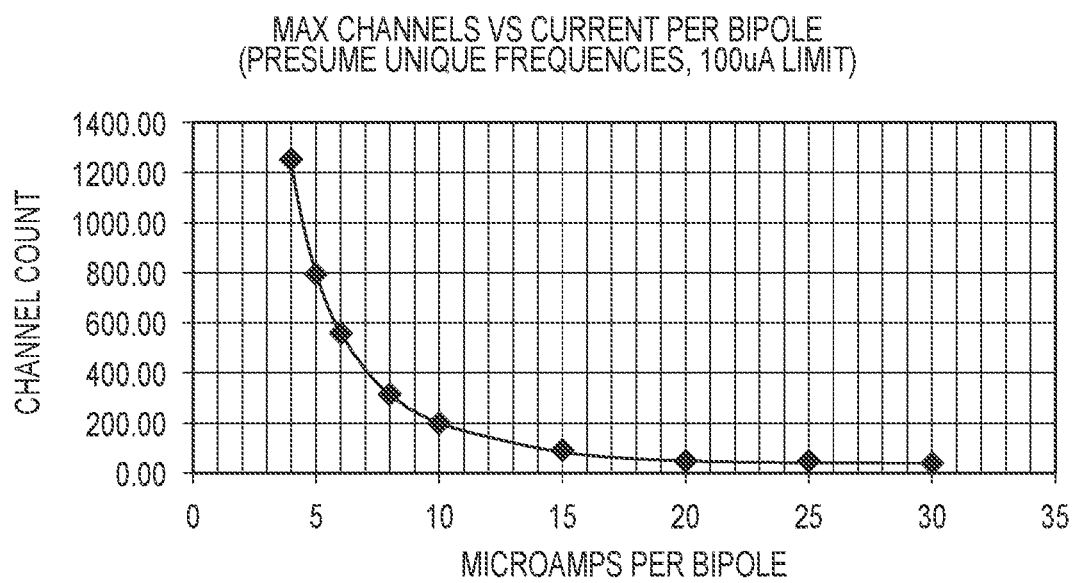
FIG. 6 is a chart illustrating a maximum number of channels vs. current.

Conversely, doubling the current per bi-pole electrode pairs reduces the maximum number of channels as a function of its square. That is, when using a 10 micro-amp drive signal per bi-pole, 200 channels would be allowed. When using a 20 micro-amp drive signal per bi-pole, 50 channels would be allowed. Stated otherwise, lowering current increases allowable channel count by a square factor while increasing current decreases allowable channel count by a square factor. FIG. 6 provides a chart that illustrates how a 100 uA limit can be achieved with different current levels per bi-pole and associated channel count. As shown, below about 15 micro-amps the number of allowable channels increases dramatically. This demonstrates the advantage of reducing the current per bi-pole. Of further note, this also allows determining a maximum drive current based on a number of bi-poles contained on or in a medical device. That is, the drive current may be maximized for a given number of bi-poles while remaining within safe sum current limits to enhance signal-to-noise ratios of response signals.

Higher unique frequencies also assist in increasing the maximum number of channels possible while maintaining safe sum current limits. For a 200 micro-amp auxiliary current limit (e.g., for frequencies 20 kHz and up), the theoretical count increases to:

$$2\left(\frac{200\ uA}{5\ uA}\right)^2 = 2(40^2) = 3200\ \text{channels} \quad (6)$$

Such a large number of channels may not be practical for many reasons but demonstrates the benefit of higher frequencies along with low drive current per bi-pole pair. In any arrangement, use of unique frequencies for the drive signals of a plurality of bi-pole electrodes significantly increases the number of bi-poles that may be interrogated to determine impedance. Alternatively, use of unique frequencies allows for increasing the magnitude of a drive current applied to the bi-poles while maintaining auxiliary current limits for a patient below a predetermined threshold.

While utilizing unique frequencies for each drive signal provides significant benefits for determining impedances of high-count electrode medical devices, the measured response signal to the drive signals must be identified for each bi-pole. The disclosed method and system utilize digital signal processing to synchronously demodulate the response signal (e.g., voltage signal) at each electrode. Another important aspect of the present disclosure is that driving each electrode pair/bi-pole at a unique frequency not only allows for significantly increasing a number of electrodes that may be interrogated and/or increasing drive current magnitudes but also minimizes crosstalk between channels.

The following discussion is directed to an exemplary embodiment of a medical device having 200 electrodes (100 bi-poles) using 100 spaced drive frequencies. By spacing these drive frequencies at exactly 25 hertz apart, the bandwidth requirement is 25×100=2500 hertz. Other frequency offsets are possible. In this example drive frequencies from 15025 Hz through 17500 are utilized. Keeping the frequencies tightly packed simplifies bandwidth requirements of the digitizing amplifier circuit. Further, each electrode pair/bi-pole is driven with a current in the 1 to 10 micro-amp range. It will be appreciated that different frequency ranges and drive currant ranges may be utilized.

Synchronous demodulation allows the unique frequencies to be detected independent of each other while minimizing crosstalk. To achieve this, the drive frequencies are made orthogonal to each other by setting the drive frequencies at harmonics of a base frequency (e.g., 25 Hz in the present example) and measuring a response over a period with an integer number of cycles. By selecting an update/sampling rate of 25 per second (e.g., 40 millisecond period), frequencies on 25 hertz boundaries will have integer number of cycles in each sampling period. That is, frequencies on 25 hertz boundaries such as 16025, 16050, 16075 hertz etc. will be orthogonal to each other. The sampling rate of 25 per second was selected as a compromise between tight frequency packing and fast response time. For cardiac application, it is noted that a heart beats in the range of 1 to 4 beats per second and 25 samples per second is capable of tracking changes due to cardiac motion. It is possible to space frequencies closer together, but the ability to track impedance changes through the cardiac cycle diminishes. Reducing the spacing by a factor of 2 to 12.5 Hz would also reduce the reporting/sampling rate to 12.5 per second and, while possible, is less than ideal for tracking the impedance changes in a rapidly beating heart. Likewise, it is possible to increase spacing and, in turn, achieve more samples per second, though bandwidth requirements increase.

Synchronous demodulation consists of multiplying the measured and digitized response signal (which is a composite of multiple frequencies) by a replica of each drive signal of exactly the same frequency and a known phase offset. The resultant signal is then low-pass filtered and decimated to (in this example) 25 samples per second. The sampling rate of the analog-to digital converter (ADC) is not critical and in fact need not meet the traditional Nyquist sampling rate. However, the amplifying circuit must have adequate bandwidth to pass the signal to the ADC. By calibrating the system and compensating for expected phase delay between drive signal and received signal, quadrature demodulation may occur. Thus, an in-phase component for resistive impedance and a quadrature component for reactive impedance may be found. This is commonly known as complex impedance. Synchronous demodulation also allows for signal extraction with very low current levels. Successful detection of impedance below 1 micro-amp has been demonstrated, though higher current levels provide better signal-to-noise ratio.

Figure 7:
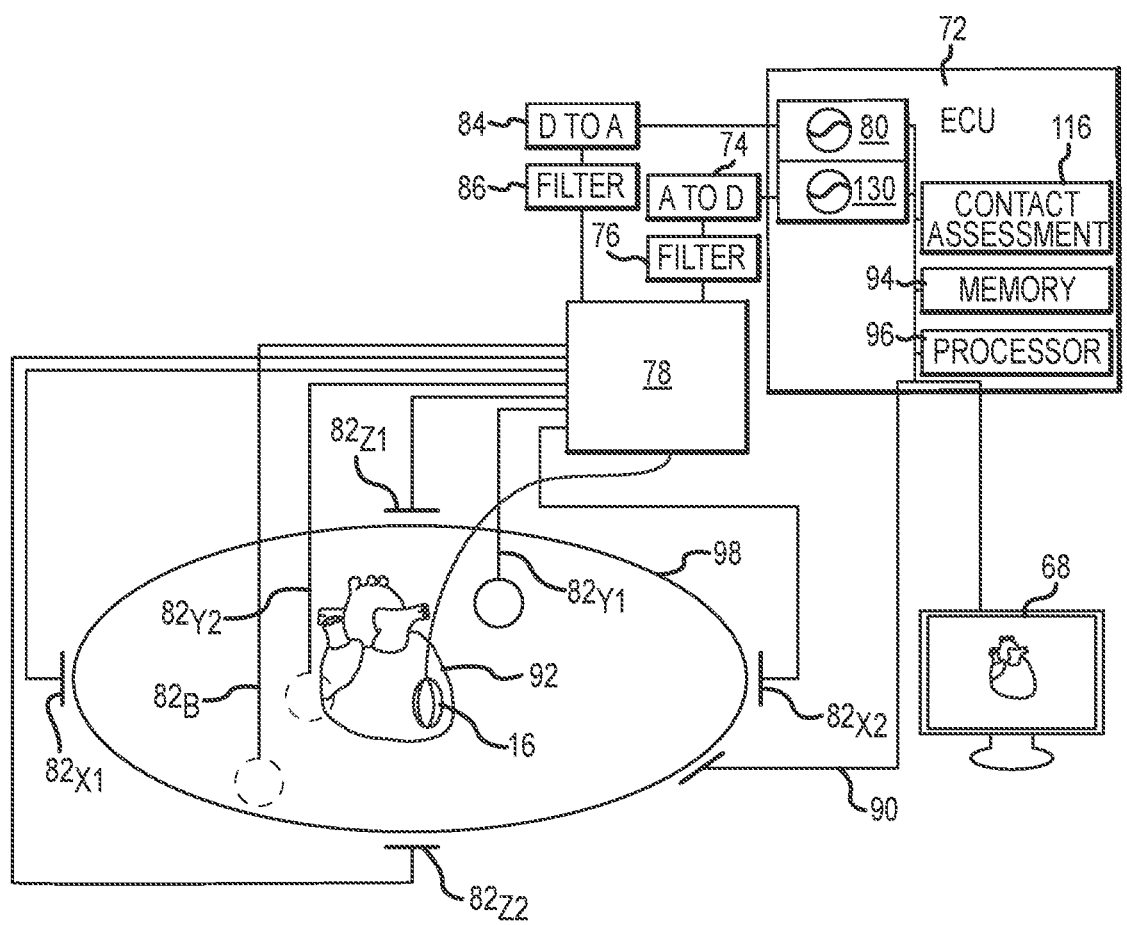
FIG. 7 is a diagrammatic depiction of an exemplary system that may include functionality for determining impedances for a plurality of pairs of electrodes on an elongate medical device.

FIG. 7 is a diagrammatic depiction of an embodiment of an exemplary mapping and navigation system 70 that be utilized with an elongated medical device 16 to, for example, determine impedance, determine contact sensing, determining the location (i.e., position and orientation) of an elongate medical device (e.g., catheter) within the body of a patient, mapping the anatomy of the patient, etc. The system 70 may include various visualization, mapping and navigation components as known in the art, including, for example, an EnSitePrecision™ system commercially available from St. Jude Medical, Inc., or as seen generally, for example, by reference to U.S. Pat. No. 7,263,397, or U.S. patent application publication no. 2007/0060833, both of which are hereby incorporated by reference in their entireties as though fully set forth herein.

The system 70 may include an electronic control unit (ECU) 72, an analog-to-digital converter (A-to-D) 74, a filter 76 (e.g., bandpass filter), a digital to analog converter 84, a filter 86 (e.g., bandpass filter), a switch 78, a signal source or signal generator 80, a demodulator circuit 130, a graphical user interface 68 and, in various embodiments, a plurality of body surface patch electrodes 82. Additional circuitry may be included as more fully discussed below. The system 70 may be electronically and/or mechanically coupled with an elongate medical device such as the 128-electrode catheter 16 of FIG. 4. The system 70 may be configured for a number of functions for guiding the elongate medical device 16 to a target site within the body of a patient 98, such as the heart 92, and for assessing contact between the elongate medical device 84 and the tissue of the patient 98. The system 70 may further include a conventional set of EGC leads 90 for the capture and measure patient ECG data. The elongate medical device may be one of the catheters 24 or 16 described herein (see FIGS. 1 and 4), or some other elongate medical device. The elongate medical device may have a plurality of pairs of electrodes.

The signal generator 80 outputs multiple excitation or drive signals for assessing an impedance of one or more electrodes. More specifically, the signal generator 80 may generate a plurality of excitation or drive signals having unique frequencies within a range from about 1 kHz to over 500 kHz, more typically within a range of about 2 kHz to 200 kHz, and even more typically between about 10 kHz and about 20 kHz, in one embodiment. The drive signals may each have a constant current, typically in the range of between 1-200 µA, and more typically about 5 µA, in one embodiment. The signal generator 80 may also generate signals involved in, for example, determining a location of the electrodes 92 within the body of the patient.

The ECU 72 may include a memory 94 and a processor 96. The memory 94 may be configured to store data respective of the elongate medical device 84, the patient 98, and/or other data (e.g., calibration data). Such data may be known before a medical procedure (medical device specific data, number of catheter electrodes, etc.), or may be determined and stored during a procedure. The memory 94 may also be configured to store instructions that, when executed by the processor 96 and/or a contact assessment module 116, cause the ECU 72 to perform one or more methods, steps, functions, or algorithms described herein. For example, but without limitation, the memory 94 may include data and instructions for determining impedances respective of one or more electrodes 92 on the elongate medical device 84. The ECU may be connected to a graphical user interface 68, which may display an output of sensed tissue (e.g., heart), the elongated medical device (not shown) and/or assessed values (e.g., impedances) for electrodes of the elongated medical device.

Figure 8:
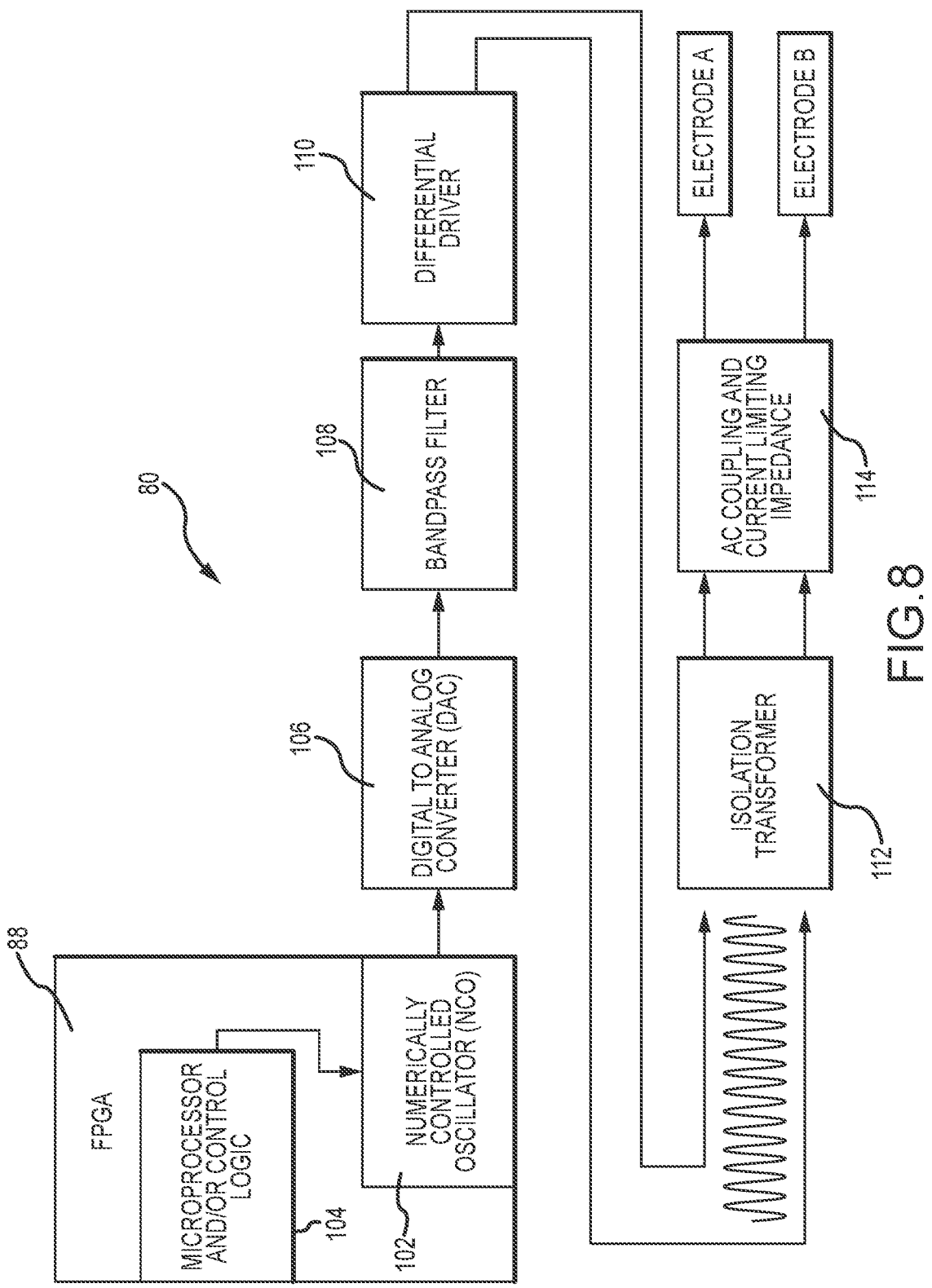
FIG. 8 is a diagrammatic depiction of one embodiment of a current source.

FIG. 8 illustrates one embodiment of a signal source 80 (e.g., current source) that provides an excitation signal for one pair of electrodes. In the present embodiment, the signal source 80 includes a field programmable gate array (FPGA) 88. However, it will be appreciated that other circuitry, including without limitation, application specific integrated chips, Altera Cyclone series or Xilinx Spartan series may be utilized. In the present embodiment, the FPGA 88 includes a numerically controlled oscillator (NCO) 102. The NCO 102 is a digital signal generator which creates a synchronous (i.e. clocked), discrete-time, discrete-valued representation of a waveform, usually sinusoidal. The NCO 102 is programmable to provide a waveform having a desired frequency, amplitude and/or phase.

In the present embodiment, the NCO 102 creates a sinusoidal waveform of a desired frequency based on an input (e.g., single fixed-frequency reference) provided from a microprocessor and/or control logic 104. In the present embodiment a microprocessor/control logic 104 is incorporated in the FPGA provides the inputs to the NCO 102. However, it will be appreciated that the NCO inputs may be provided by, for example, the processor 96 of the ECU 72. In any arrangement, the NCO 102 generates a digital waveform output having a desired frequency (e.g., unique frequency). The output of the NCO is received by a digital to analog converter (DAC) 106, which converts the received digital signal to a corresponding analog signal. A bandpass filter 108 is utilized to smooth the converted analog signal. A differential driver (e.g., op amp) 110 receives the smoothed analog signal from the bandpass filter 108 and sends the same signal as a differential pair of signals, each in its own conductor to an isolation transformer 112. Provided that impedances in the differential signaling circuit (e.g., differential driver and isolation transformer) are equal, external electromagnetic interference tends to affect both conductors identically. As the receiving circuit (isolation transformer) only detects the difference between the conductors, the technique resists electromagnetic noise compared to a one conductor arrangement. The isolation transformer 112 transfers AC current of the signals originating from the source 80 to the electrodes A and B of the medical device while isolating the medical device from the source. The isolation transformer 112 blocks transmission of DC components in the signals from passing to the electrodes while allowing AC components in signals to pass. The dual output from the isolation transformer 112 is received by AC coupler 114 (e.g., capacitor) that further limit low frequency current from passing to the electrodes. The AC coupler outputs the signals to the electrodes A and B of the electrode pair (e.g., bi-pole). The AC coupler 114 has an impedance that is orders of magnitude greater than the impedance across the electrodes A and B.

Figure 9:
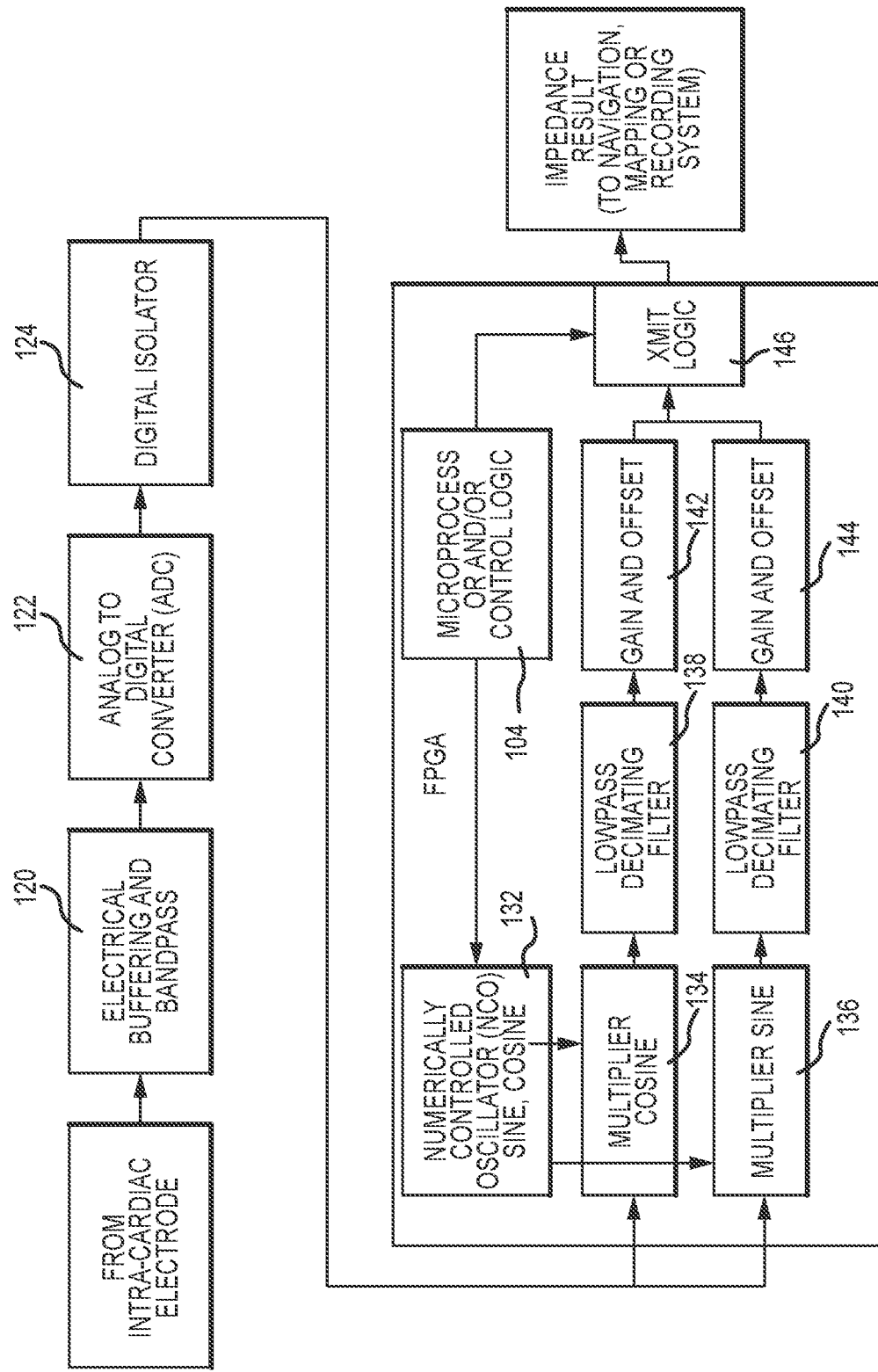
FIG. 9 is a diagrammatic depiction of one embodiment of a measurement circuit and demodulation circuit.

FIG. 9 illustrates one embodiment of a signal measuring circuit (e.g., signal sampler) and a synchronous demodulation circuit. Initially, a response signal from one of the electrodes A or B is received at a filter 120 (e.g., buffer amplifier) that transfers a current from the electrode, which has a low output impedance level, to an analog to digital converter (ADC) 122, which typically has a high input impedance level. The buffer amplifier prevents the second ADC from loading the current of electrode circuit and interfering with its desired operation. The ADC 122 samples the received analog signal at a known sampling rate (e.g., 64 k/s) and converts the analog response signal to a digital response signal. In the present embodiment, an output of the ADC passes through a digital isolator 124, which transfers the digital response signal to the control system (e.g., ECU) while isolating the control system from the medical device.

The digital response signal passes to a synchronous demodulator circuit 130 which, in the present embodiment, is defined in the same FPGA utilized for the signal source 80. As noted, synchronous demodulation consists of multiplying a digitized response signal by a replica of a drive signal of exactly the same frequency and a known phase offset. That is, a demodulation signal having the same frequency as the drive signal and a known phase offset from the drive signal is generated and multiplied with the digitized response signal. Generating the demodulation signal(s) using the same FPGA 88 that generates the drive signal(s) simplifies the demodulation process. However, it will be appreciated that this is not a requirement and that the synchronous demodulator circuit and the signal source may be separate and/or formed of different software and/or hardware components. In any arrangement, the synchronous demodulation circuit must be able to replicate the drive signal for a given frequency.

In the illustrated embodiment, the digital response signal is split as it is received by the synchronous demodulator circuit 130. A numerically controlled oscillator (NCO) 132 generates sine and cosine representations of the corresponding drive signals. Each signal is adjusted with a phase delay such that the cosine signal aligns with the in-phase (e.g. resistive) component based on an input provided from the microprocessor and/or control logic 104. The split digital response signals are multiplied point-by-point by the sine and cosine signals in sine and cosine multipliers 134, 136, respectively. This yields in-phase and quadrature channels. The channels are filtered and decimated by low pass decimating filters 138, 140, which in the present embodiment are formed of cascaded integrator-comb (CIC) filters. Following the example above, where the drive signal is a harmonic of a 25 Hz base frequency, the channels/signals are decimated to 25 samples per second such that each decimated signal has an integer number of cycles. The decimated signals then pass through a gain and offset calibration 142, 144 to compensate for expected hardware variations and to scale the result to resistive and reactive impedance in units of ohms. This information may then be transmitted, for example, via an output port 146 to, for example, the ECU. The above noted measuring and demodulation process may be performed for the responses of both electrodes A and B.

Figure 10:
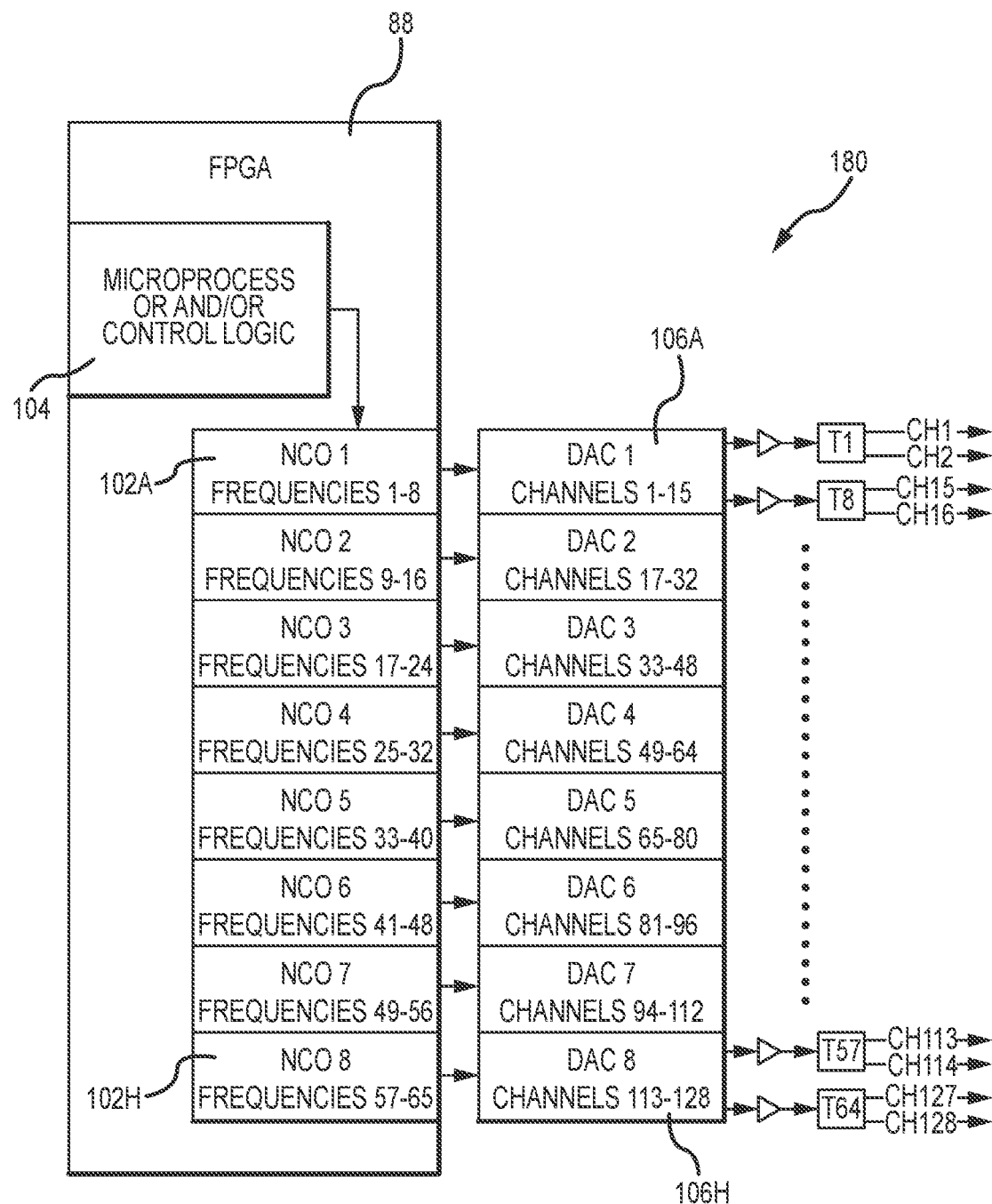
FIG. 10 is a diagrammatic depiction of an embodiment of a current source configured to provide a plurality of drive signals to electrodes of a medical device.

In order to accommodate a plurality of electrodes, the systems and processes of FIGS. 8 and 9 may be scaled. FIG. 10 illustrates an embodiment of a signal source 80 (e.g., current source) scaled to provide a plurality of unique frequency excitation/drive signals for a plurality of electrode pairs/bi-poles. In the illustrated embodiment, the current source 80 provides 64 unique frequencies to 128 total electrodes (i.e., 64 electrode pairs/bi-poles). It will be appreciated that this embodiment is provided by way of example and not by way of limitation. Along these lines, unique frequency drive signals may be provided for more or fewer frequencies and/or electrodes. Similar to the signal source described above in relation to FIG. 8, the signal source 80 is defined within a field programmable gate array (FPGA) 88. The FPGA 88 further includes a plurality of numerically controlled oscillators (NCOs) 102a-h (hereafter NCO 102 unless specifically referenced). As above, the NCOs 102 receive a reference signal input from a micro-compressor and/or control logic 104. In the illustrated embodiment, each NCO 102 has eight channels. That is, each NCO 102 is programmable to provide eight unique frequencies. In this regard, the eight NCOs 102a-h are operative to provide 64 unique frequencies. Continuing with the previous example, each NCO provides eight unique frequencies spaced on 25 Hz intervals. Collectively, the NCOs 102a-h provide 64 individual frequencies between approximately 16 kHz and 18 kHz. The output of each NCO 102 is received by a digital to analog converter (DAC) 106a-h. Each DAC has eight independent channels each configured to generate an analog representation of a received drive signal frequency for receipt by the electrodes of an attached medical device. Similar to the source described in relation to FIG. 8, the output of the DAC's may be received by bandpass filters, differential drivers and/or transformers prior to being applied to individual electrodes of the medical device.

Figure 11:
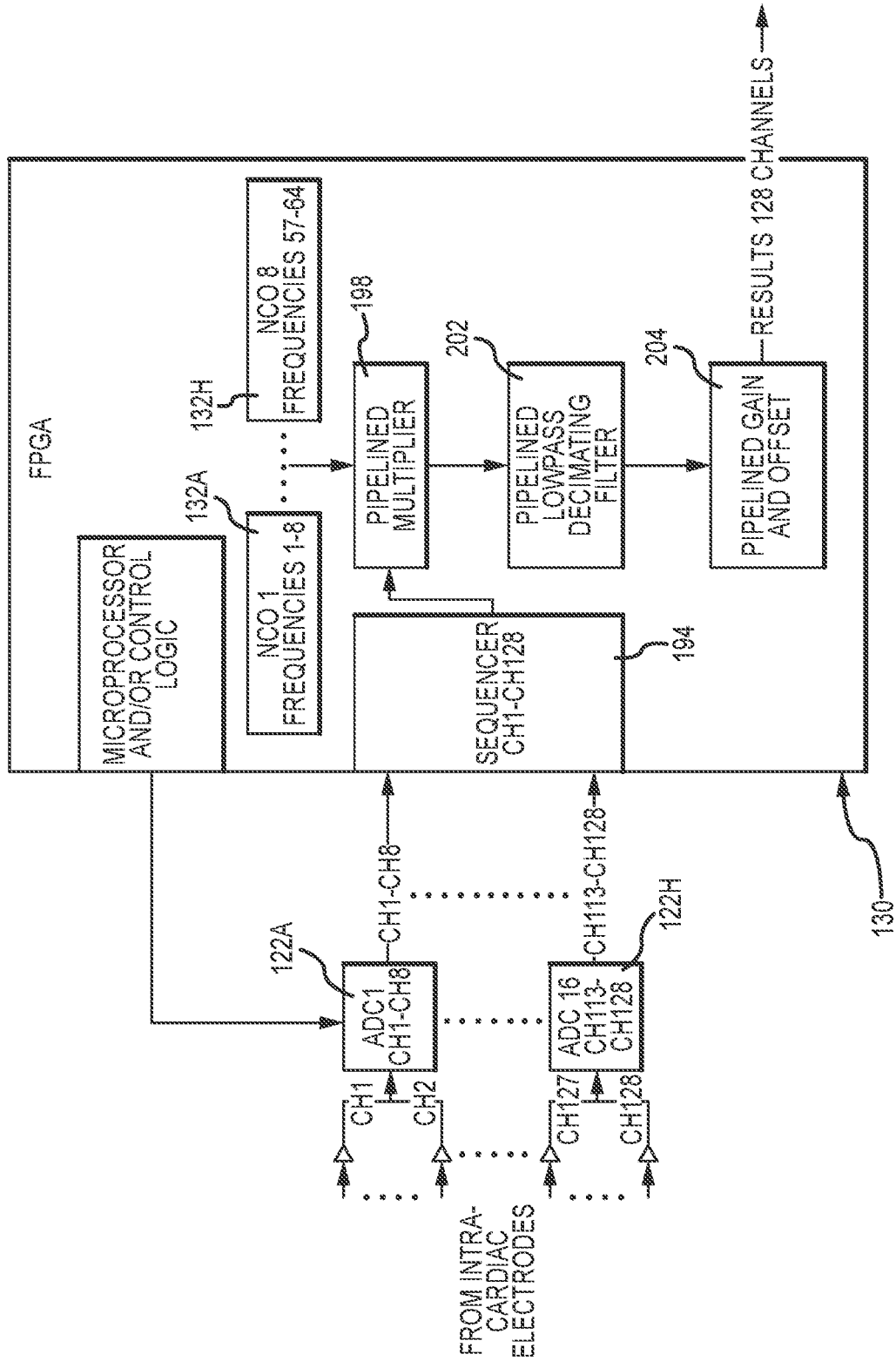
FIG. 11 is a diagrammatic depiction of an embodiment of a measurement circuit and demodulation circuit configured to measure and demodulate responses from a plurality of electrodes of a medical device.

FIG. 11 illustrates one embodiment of a multi-channel signal measuring circuit and multi-channel synchronous demodulation circuit. The overall operation of the embodiment of FIG. 11 is similar to the operation of the embodiment of FIG. 9. Initially, response signals from the electrodes are received at a filter (e.g., buffer amplifier) that transfers a current from the electrodes to analog to digital converters (ADCs) 122a-h (hereafter 122 unless specifically referenced). As with the DAC's of the signal source, the measurement circuit utilizes NCOs to generate sine and cosine signals for synchronous demodulation corresponding to each electrode's driven frequency.

A synchronous demodulator circuit 130 receives the digital response signals from the ADCs 122. In the present embodiment, the synchronous demodulator circuit 130 is defined in the same FPGA utilized for the signal source 80. More specifically, the digital signals are received by a 128-channel sequencer 194 which samples all the signals at one point time and provides the sampled signals to a pipelined multiplier 198. The pipelined multiplier is in communication with a plurality of NCOs 132a-h, which again generate appropriately phase delayed sine and cosine representations of each unique frequency drive signal based on inputs from the microprocessor and/or control logic 104. The pipelined multiplier 198 operates in a manner that is substantially identical to the multipliers described above in relation to FIG. 9 with the exception that pipelining allows the calculations of all channels utilizing a single instantiation of demodulator circuit 130. The pipelined multiplier 198 multiplies each response by respective sine and cosine demodulation signals. The output of the pipeline multiplier 198 is provided to a pipelined low pass decimating filter 202, which samples the outputs over an integral number of cycles, as described above. The decimated signals then pass through pipelined gain and offset calibration 204 to convert to units of ohms impedance. Thus, a real component of resistive impedance and an imaginary component of reactive impedance may be found for each of the 128 electrodes. This information may then be transmitted to the ECU.

Figure 12:
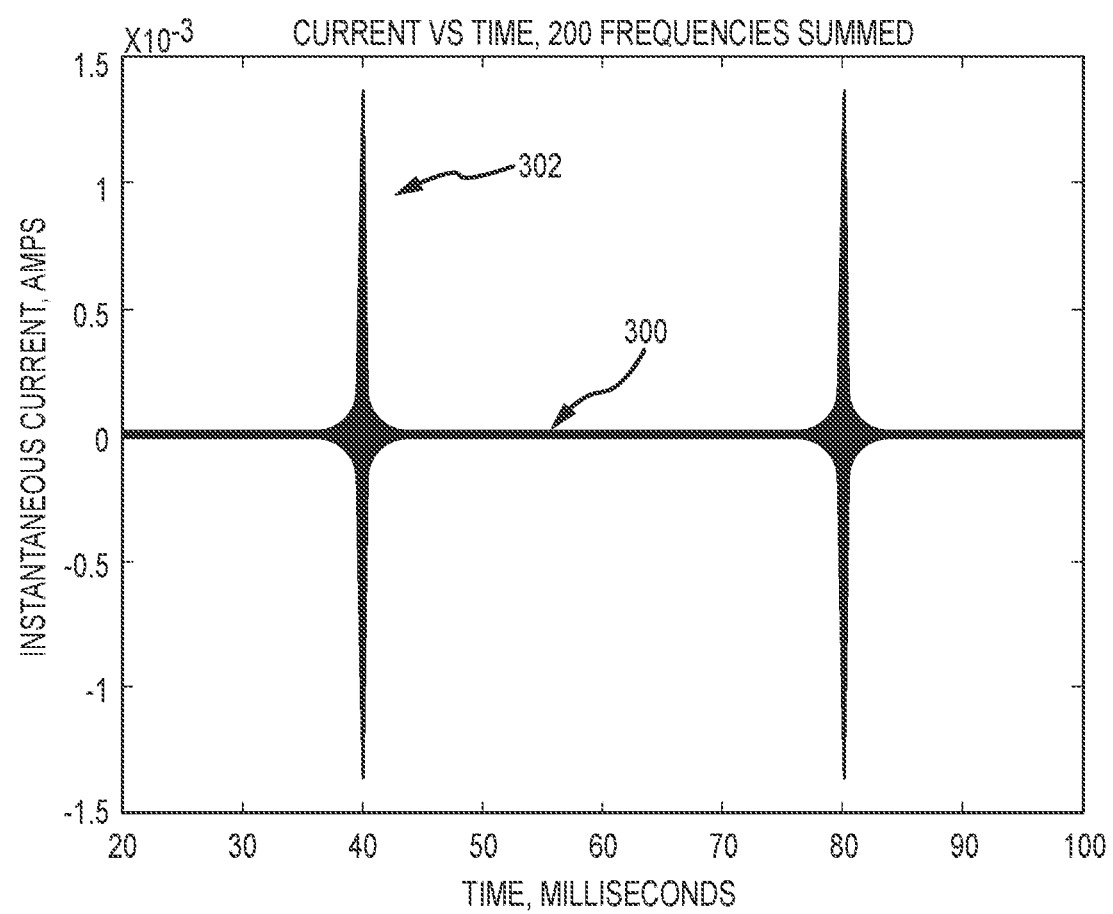
FIG. 12 is a chart illustrating a sum current of a plurality of harmonic frequencies.

The systems and processes of FIGS. 8-11 allow for synchronous demodulation of a large number of electrodes when the drive signals are orthogonal (i.e., unique drive frequencies at harmonics of a base frequency and responses are measured over a period with an integer number of cycles). Further, the use of multiple unique drive frequencies allows increasing the drive current as the RMS (root mean square) value of the resultant signal increases with the square root of the number of channels. What is not obvious is the signals may add in a manner that creates a large peak value periodically when all the frequencies come into phase. One aspect of the synchronous demodulation scheme is the frequencies are not random but are chosen to be separated by a fixed amount. As such, if all the frequencies start at time zero and are on 25 Hz boundaries (or other equal boundaries), every 40 milliseconds (25 times per second) all signals will be nearly in phase and a large instantaneous peak value results. This is shown graphically in FIG. 12 which shows a trace of a sum current 300 where 200 frequencies starting at 16025 Hz and every 25 Hz thereafter to 19500 Hz are added together. Mathematically, the RMS current in this case of 200 frequencies at 5 micro-amps is (5×√200) or about 70 micro-amps. However, there is a peak 302 in the sum current 300 of about 1 milliamp every 40 milliseconds. Such a peak current would be expected to exceed an auxiliary current limit/thresholds. This can be countered by adding a random (non-uniform) phase offset to each channel. This minimizes the peaking and spreads the current over time. The sum current 400 with each channel assigned a random phase, is illustrated in FIG. 13.

Figure 13:
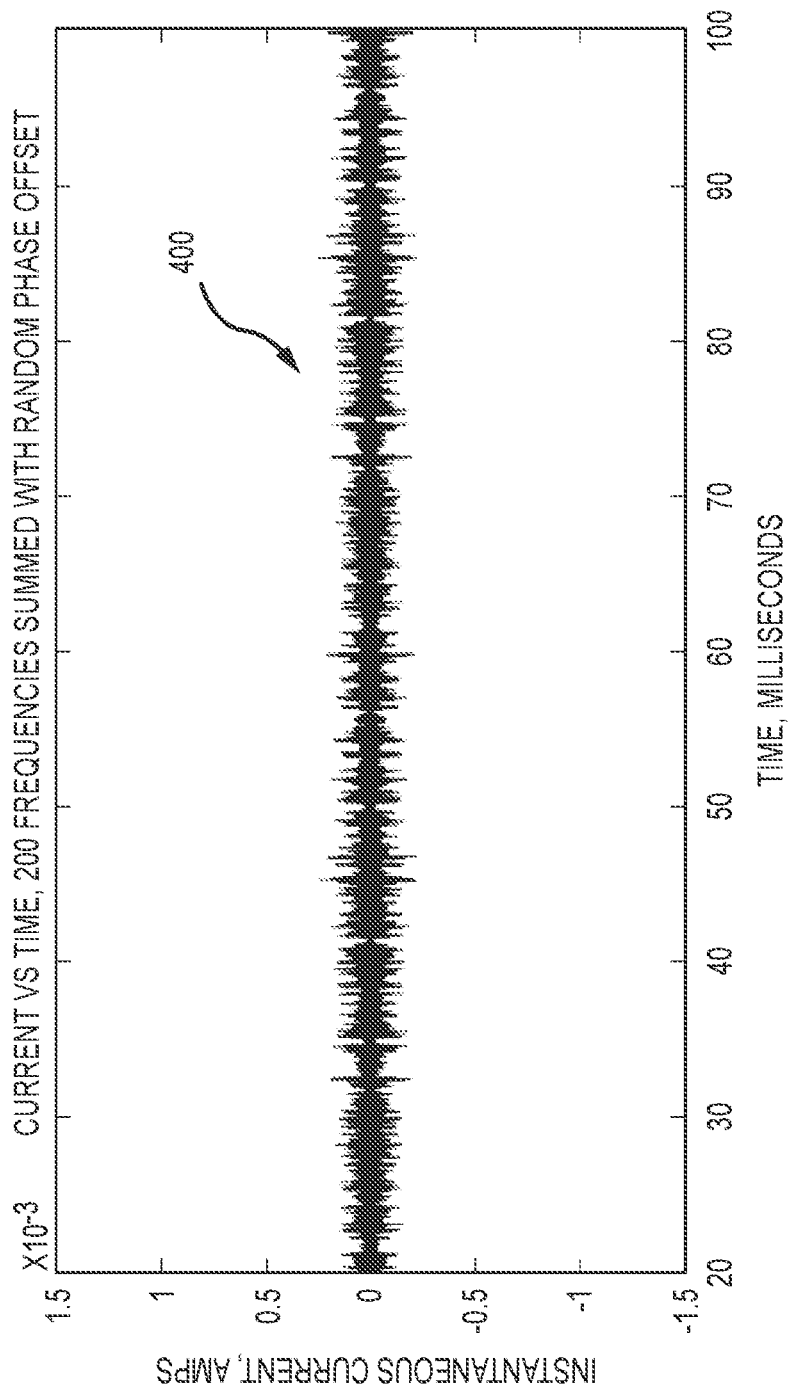
FIG. 13 is a chart illustrating a sum current when a plurality of harmonic frequencies have random phase offsets.

As shown in FIG. 13, when random phase offsets are applied to each drive signal, the sum current 400 is much more uniform and lower in peak current. The addition of phase offset to each frequency of the drive signals does not hinder the synchronous demodulation as the drive signals remain orthogonal at 25 Hz apart. The phase offset is compensated during demodulation by simply phase delaying each input (e.g., reference frequency) in the FPGA as necessary at calibration time. This is facilitated by the use of separate NCOs for the signal source and demodulation circuit, which have both frequency and phase inputs. The source NCOs are assigned a one-time random phase offset that may be stored by the ECU and/or the FPGA. The demodulation NCOs are assigned a respective phase offset during a one-time calibration that compensates for the source NCO phase offset plus any phase delay between source NCO 102 and analog-to-digital convertor 122. Said calibration data is likewise stored by the ECU and/or FPGA.

Figure 14:
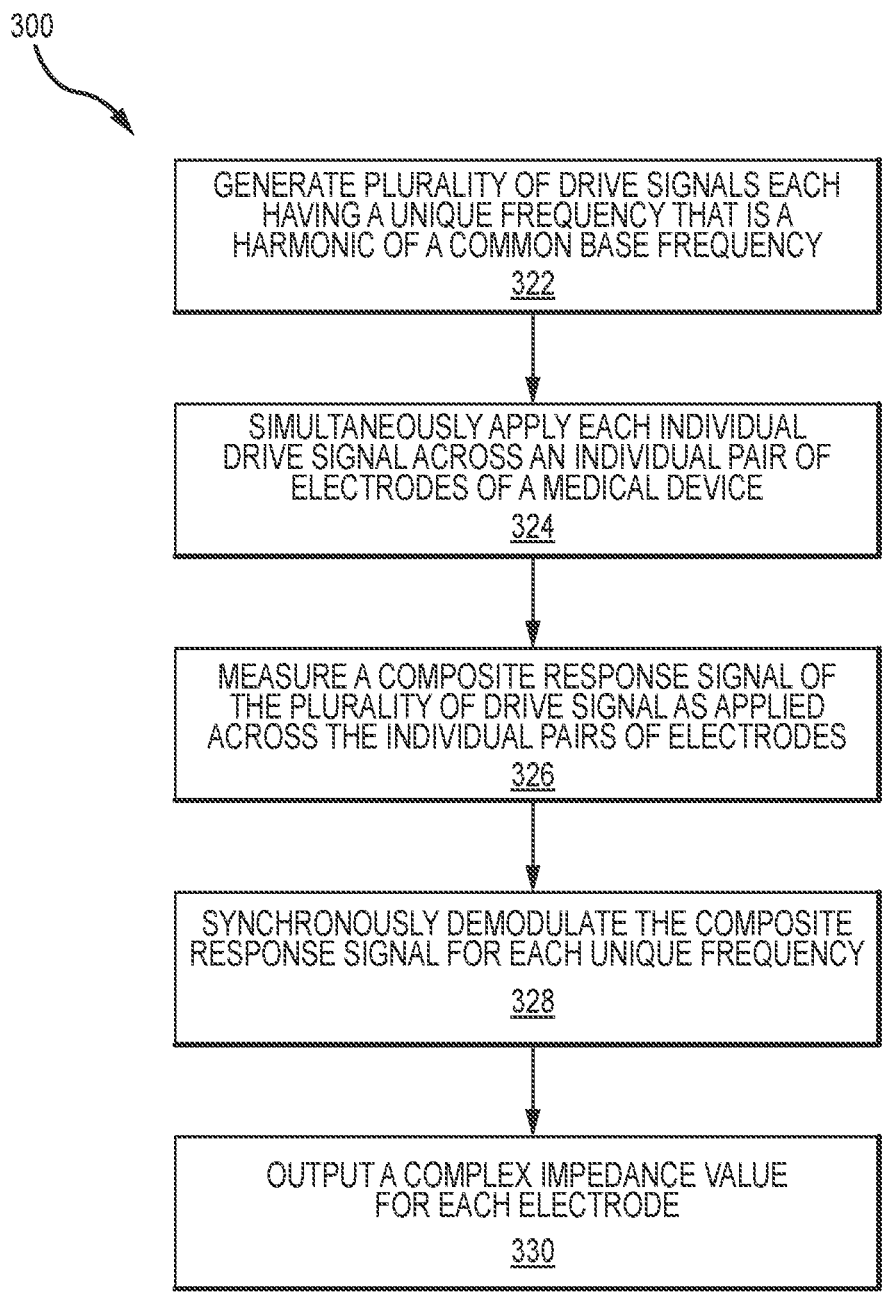
FIG. 14 is a flow chart illustrating a process for use with the disclosed systems.

FIG. 14 illustrates a process 320 that may be performed by the systems described above. Initially, the process includes generating 322 a plurality of drive signals each having a unique frequency that is a harmonic of a common base frequency. The generation of such a plurality of drive signals may further entail assigning each drive signal a random phase offset. Once the drive signals are generated, the drive signals are simultaneously applied 324 across individual pairs of electrodes of a medical device. The application of the drive signals may further include digital to analog conversion of the drive signals prior to their application to the electrodes. One or more composite response(s) of the electrodes to the drive signals is measured 326. The measurement may further entail converting analog responses of the electrodes to digital signals. The digital signals are then synchronously demodulated 328. The synchronous demodulation entails generating demodulation signals for each unique frequency. Each demodulation signal will have the same frequency and a known phase offset for a corresponding drive signal. If each drive signal has a random phase offset, the corresponding demodulation signals will have the same additional random phase offset. The synchronous demodulation of the drive signals may also include sampling the signals over a time period that includes an integer number of cycles for the drive signals. The synchronous demodulation outputs 330 a complex impedance value for each electrode. That is, a real impedance value and a reactive impedance value may be output for each electrode. For instance, these outputs may be output to the graphical user interface 68 (see FIG. 7). Along these lines, the assessed value for each electrode may be displayed on the graphical user interface 68 along with a graphical depiction of the catheter to provide a user with feedback on the contact status of each electrode. That is, the impedance values may be utilized for, among other things, to assess electrode contact with tissue.

Figure 15:
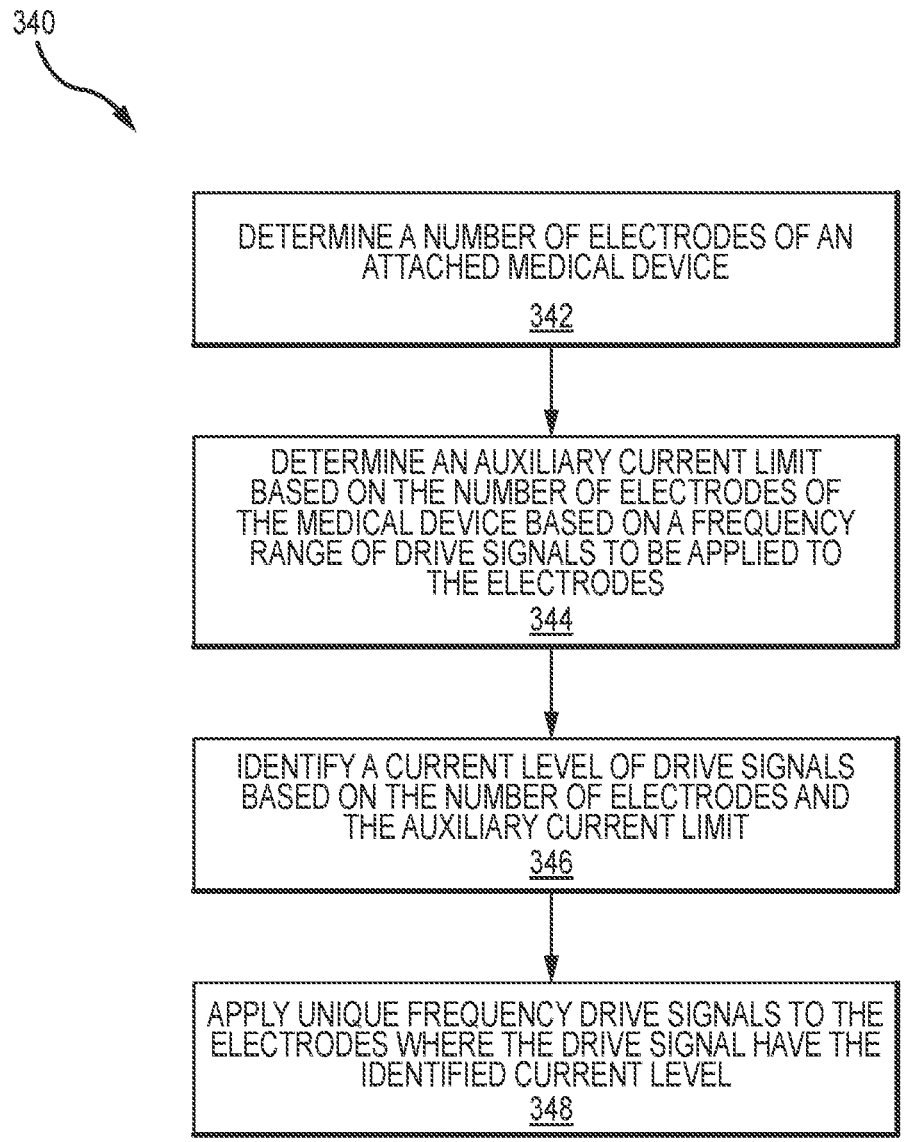
FIG. 15 is a flow chart illustrating another process for use with the disclosed systems.

FIG. 15 illustrates a further process 340 that may be performed by the systems described above. The process allows for dynamically adjusting current levels of drive signals applied to a plurality of electrodes of a medical device. Initially, the process includes determining 342 a number of electrodes of an attached medical device. Such determination may be performed by a control unit (e.g., ECU) interrogating the attached medical device. Alternatively, a system user may input this information. Based on the number of electrodes and a frequency band for a plurality drive signals that will be applied to the electrodes, an auxiliary current limit or threshold is determined 344. The auxiliary current limit may be determined from stored data (e.g., calibration data). Based on the auxiliary current limit and the number of electrodes, a current level may be identified 346 for drive signals that will be applied to electrodes. For instance, the current level of the drive signals may be maximized to enhance the signal-to-noise response of the signals when applied to the electrodes while maintaining a sum current of the drive signals below the auxiliary current limit. Once the current level for the drive signals is identified, unique frequency drive signals are applied 348 to the electrodes where each drive signal has identified current level.

The systems described above provides further benefits for use with medical devices. For instance, utilization of the DACs to generate the drive signals provides a means for deactivating a channel. In this regard, simply setting a DAC to zero or a static value effectively turns off a channel. Along these lines, channels may be purposefully deactivated to permit increased current levels for drive signals if needed. Another benefit is provided by the bandpass filters. As the bandpass filters only permit passage of a narrow frequency range, any software or hardware errors that result in outputting a drive signal of too low a frequency is not passed. The bandpass filters thus provide a fail-safe limit to the drive signals.

In addition to impedance calculations and contact state determinations, the system 70 may be configured to determine the position and orientation (P&O) of an elongate medical device 16 (e.g., of a distal end portion of a catheter) within the body of the patient 98. Accordingly, the ECU 72 may be configured to control generation of one or more electrical fields and determine the position of one or more electrodes 92 within those fields. The ECU 72 may thus be configured to control signal generator 80 in accordance with predetermined strategies to selectively energize various pairs (dipoles) of body surface patch electrodes 82 and catheter electrodes.

Referring again to FIG. 7, a mapping and navigation functionality of the system 70 will be briefly described. The body surface patch electrodes 82 may be used to generate axes-specific electric fields within the body of the patient 98, and more specifically within the heart 92. Three sets of patch electrodes may be provided: (1) electrodes $82_{X1}$, $82_{X2}$, (X-axis); (2) electrodes $82_{Y1}$, $82_{Y2}$, (Y-axis); and (3) electrodes $82_{Z1}$, $82_{Z2}$, (Z-axis). Additionally, a body surface electrode ("belly patch") $82_B$, may be provided as an electrical reference. The body patch electrodes $82_{X1}$, $82_{X2}$, $82_{Y1}$, $82_{Y2}$, $82_{Z1}$, $82_{Z2}$, $82_B$ may be referred to herein generically as a body patch electrode 82 or as the body patch electrodes 82. Other surface electrode configurations and combinations are suitable for use with the present disclosure, including fewer body patch electrodes 82, more body patch electrodes 82, or different physical arrangements, e.g. a linear arrangement instead of an orthogonal arrangement.

Each patch electrode 82 may be independently coupled to the switch 78, and pairs of patch electrodes 82 may be selected by software running on the ECU 72 to couple the patch electrodes 82 to the signal generator 80. A pair of electrodes, for example the Z-axis electrodes $82_{Z1}$, $82_{Z2}$, may be excited by the signal generator 80 to generate an electrical field in the body of the patient 86 and, more particularly, within the heart 88. In an embodiment, this electrode excitation process occurs rapidly and sequentially as different sets of patch electrodes 82 are selected and one or more of the unexcited surface electrodes 82 are used to measure voltages. During the delivery of the excitation signal (e.g., current pulse), the remaining (unexcited) patch electrodes 82 may be referenced to the belly patch $82_B$ and the voltages impressed on these remaining electrodes 82 may be measured. In this fashion, the patch electrodes 82 may be divided into driven and non-driven electrode sets. A low pass filter may process the voltage measurements. The filtered voltage measurements may be transformed to digital data by the analog to digital converter and transmitted to the ECU 72 for storage (e.g. in the memory 94) under the direction of software. This collection of voltage measurements may be referred to herein as the "patch data." The software may store and have access to each individual voltage measurement made at each surface electrode 82 during each excitation of each pair of surface electrodes 82.

Generally, in an embodiment, three nominally orthogonal electric fields may be generated by the series of driven and sensed electric dipoles in order to determine the location of the elongate medical device 16 (i.e., of one or more electrodes). Alternately, these orthogonal fields can be decomposed and any pair of surface electrodes (e.g., non-orthogonal) may be driven as dipoles to provide effective electrode triangulation.

The patch data may be used, along with measurements made at one or more electrodes catheter electrode and measurements made at other electrodes and devices, to determine a relative location of the one or more catheter electrodes. In some embodiments, electric potentials across each of the six orthogonal patch electrodes 82 may be acquired for all samples except when a particular surface electrode pair is driven. In an embodiment, sampling electric potentials may occur at all patch electrodes 82, even those being driven.

As a part of determining locations of various electrodes, the ECU 72 may be configured to perform one or more compensation and adjustment functions, such as motion compensation. Motion compensation may include, for example, compensation for respiration-induced patient body movement, as described in U.S. patent application publication no. 2012/0172702, which is hereby incorporated by reference in its entirety.

Data sets from each of the patch electrodes 82 and the catheter electrodes are all used to determine the location of the catheter electrodes within the patient 98. After the voltage measurements are made for a particular set of driven patch electrodes 82, a different pair of patch electrodes 82 may be excited by the signal generator 80 and the voltage measurement process of the remaining patch electrodes 82 and catheter electrodes takes place. The sequence may occur rapidly, e.g., on the order of 100 times per second in an embodiment. The voltage on the catheter electrodes within the patient 98 may bear a linear relationship with the position of the electrodes between the patch electrodes 82 that establish the electrical fields, as more fully described in U.S. Pat. No. 7,263,397, which is hereby incorporated by reference in its entirety.

In summary, FIG. 7 shows an exemplary system 70 that employs seven body patch electrodes 82, which may be used for injecting current and sensing resultant voltages. Current may be driven between two patches 82 at any time. Positioning measurements may be performed between a non-driven patch 82 and, for example, belly patch $82_B$ as a ground reference. The position of an electrode 92 may be determined by driving current between different sets of patches and measuring one or more impedances. Some impedances that may be measured may be according to currents driven between pairs or sets of two catheter electrodes on the elongate medical device 16. In one embodiment, time division multiplexing may be used to drive and measure all quantities of interest. Position determining procedures are described in more detail in, for example, U.S. Pat. No. 7,263,397 and publication no. 2007/0060833 referred to above.

As previously noted, impedance values may be utilized to assess contact between an electrode and patient tissue. Along these lines, measuring the impedance of an electrode has been demonstrated to provide a reliable method of detecting when that electrode comes in contact with, for example, intercardiac tissue. Specifically, due to the reduced conductivity of intercardiac tissue compared to blood, the impedance of an electrode is significantly higher once it comes in contact with the tissue. Accordingly, the electrode impedances determined above may be utilized to provide an indication of tissue contact.

Figure 16A:
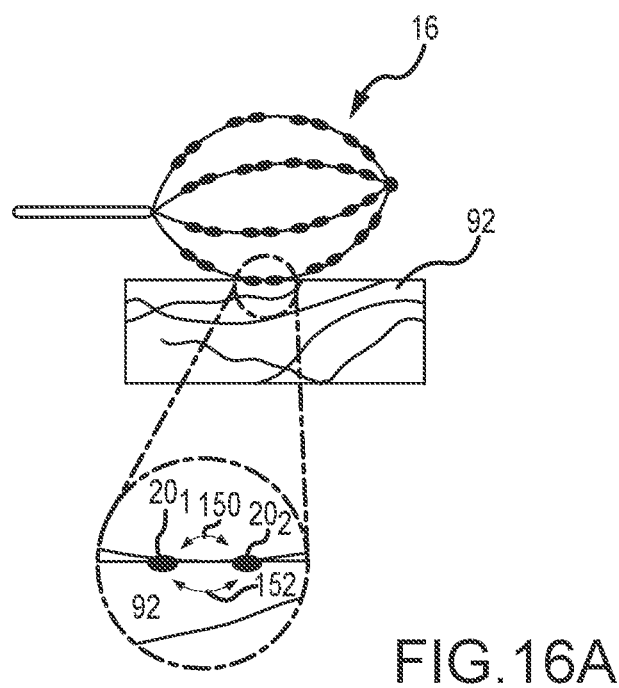
FIG. 16A illustrates a medical device contacting patient tissue.

During a procedure, the impedance at an electrode-tissue interface, which is indicative of proximity or contact, may be measured before, during and/or after tissue contact using the measurement circuit discussed above and/or the contact assessment module 112 (see FIG. 7). The measured impedance, its resistive, reactance and/or phase angle components or combination of these components may be used to determine a proximity or contact condition of one or all electrodes. The proximity or contact condition may then be conveyed to the user in real-time for achieving, for example, a desired level of contact and/or an indication of lesion formation. Assessing a proximity or contact condition between an electrode of a medical device and target tissue based on impedance measurements at the electrode-tissue interface may be better understood with reference to FIGS. 16A and 16B, which show a model of an exemplary elongated medical device 16 contacting tissue. As shown, in the illustrated embodiment, the elongated medical device 16 is a basket type electrode catheter having at least a first pair of electrodes $20_1$ and $20_2$ in contact with target tissue 92 (e.g., cardiac tissue). The electrodes $20_1$ and $20_2$ are electrically connected to a signal source (e.g., signal source 80; see FIG. 7). Upon application of a drive signal between the electrodes $20_1$ and $20_2$, a circuit may be completed between the electrodes such that current flows through blood and/or patient tissue 92 (e.g., myocardium) as illustrated in FIG. 16A by arrows 150 and 152. The passage of at least a portion of the current through the patient tissue at the electrode-tissue interface affects the inductive, capacitive, and resistive effects of the electrode response to the drive signal(s). That is, the tissue contact affects the impedance measurements of the electrodes.

Figure 16B:
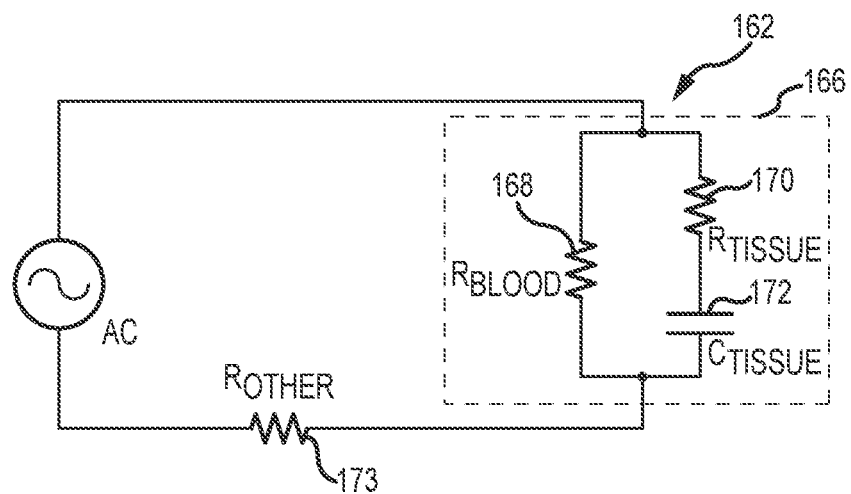
FIG. 16B illustrates a simplified electrical circuit of FIG. 16A.

The tissue contact model shown in FIG. 16A may be further expressed as a simplified electrical circuit 162, as shown in FIG. 16B. For drive signal frequencies utilized for proximity or contact assessment, capacitance and resistance at the blood-tissue interface dominate impedance measurements. Accordingly, capacitive-resistive effects at the blood-tissue interface may be represented in circuit 162 by an exemplary resistor-capacitor (R-C) circuit 166. The exemplary R-C circuit 166 may include a resistor 168 representing the resistive effects of blood on impedance, in parallel with a resistor 170 and capacitor 172 representing the resistive and capacitive effects of the target tissue 92 on impedance. When an electrode $20_1$ or $20_2$ has no or little contact with the target tissue 92, resistive effects of the blood affect the R-C circuit 166, and hence also affect the impedance measurements. As the electrode $20_1$ or $20_2$ is moved into contact with the target tissue 92, however, the resistive and capacitive effects of the target tissue 92 also affect the R-C circuit 166, and hence also affect the impedance measurements.

The effects of resistance and capacitance on impedance measurements may be better understood with reference to a definition of impedance. Impedance (Z) may be expressed as:

$$Z = R + jX \quad (7)$$

where:
R is resistance from the blood and/or tissue;
j an imaginary number indicating the term has a phase angle of +90 degrees; and
X is reactance from both capacitance and inductance.

It is observed from the above equation that the magnitude of the reactance component responds to both resistive and capacitive effects of the circuit 162. This variation corresponds to the level of contact at the electrode-tissue interface, and therefore may be used to assess the electrode-tissue coupling. By way of example, when an electrode is operated is primarily in contact with the blood, the impedance is largely resistive, with a small reactive (X) contribution. When the electrode contacts the target tissue the magnitudes of both the resistive and reactive components increase.

Alternatively, proximity or contact conditions may be determined based on phase angle. Indeed, determining proximity or contact conditions based on the phase angle may be preferred in some applications because the phase angle is represented as a trigonometric ratio between reactance and resistance. In an exemplary embodiment, the phase angle may be determined from the impedance measurements. That is, impedance may be expressed as:

$$Z = |Z| \angle \phi \quad (8)$$

where:
|Z| is the magnitude of the impedance; and
$\phi$ is the phase angle.

The phase angle also corresponds to the level of proximity or contact at the electrode-tissue interface, and therefore may be used to assess the electrode-tissue proximity or contact.

While impedance values may be utilized to assess electrode tissue contact or proximity, such assessments are typically based on an observed change in an impedance value of an electrode. That is, a measured impedance of an electrode is typically compared to a benchmark or baseline impedance value for that electrode. Accordingly, one known baselining procedure is to measure an initial impedance of an electrode in a blood pool and utilize this initial impedance as a baseline value for subsequent contact determination/comparison. Often, such a baselining or calibration procedure is performed in-vivo at the beginning of a procedure. That is, actual baseline values (e.g., empirical values) are often measured as opposed to relying on predetermined baseline data. However, predetermined (e.g., stored) baseline values may be used. One benefit of performing an in-vivo calibration is that such a procedure accounts for differences that may exist between patients and/or the physical configuration of a specific system. That is, impedance measurements are affected by catheter cabling, electrode size, and any electrode imperfections (e.g., $R_{other}$ 173; FIG. 16B). Because of this, in-vivo 'baselining' or 'calibration' procedures are most commonly used to establish baseline impedances for the electrodes such that subsequent impedance changes can be identified.

Figure 17A:
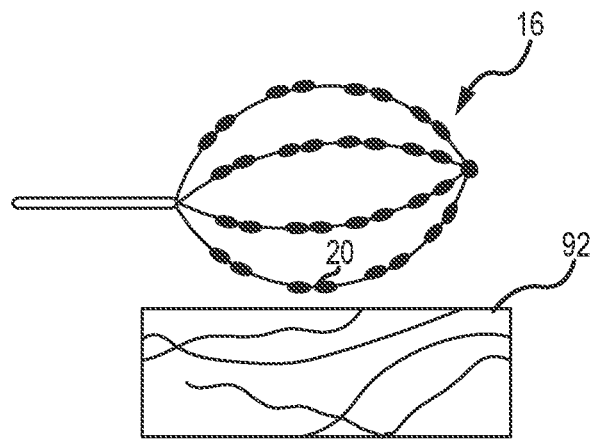
FIGS. 17A-17C illustrate three levels of contact between a medical device and patient tissue.
Figure 17B:
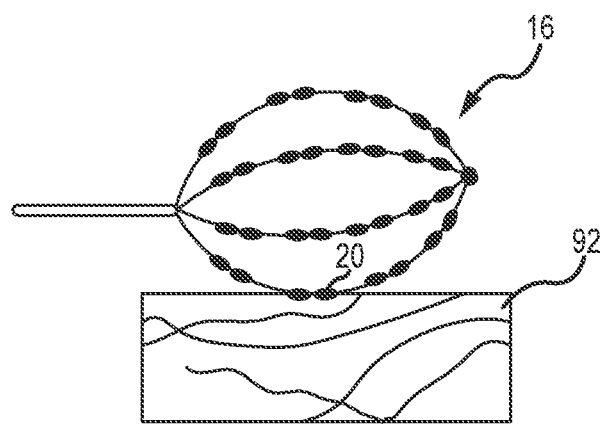
Figure 17C:
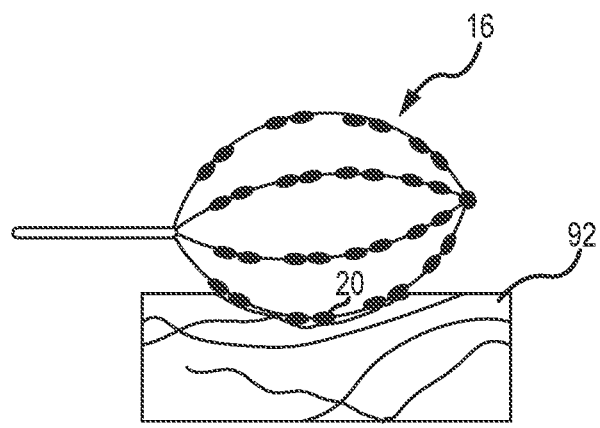

Once a baseline impedance value is established for an electrode, subsequent impedance changes for that electrode may be utilized to assess a level of tissue contact and/or tissue proximity. FIGS. 17A-17C illustrate exemplary levels of tissue contact or proximity between an electrode 20 of a medical device 16 and patient tissue 92 that may be determined from a change in impedance. Exemplary levels of contact or proximity may include "little or no contact" as illustrated by the contact condition illustrated in FIG. 17A, "light to medium contact" as illustrated by contact condition illustrated in FIG. 17B, and "hard contact" as illustrated in FIG. 17C. In an exemplary embodiment, the assessment may be output to, for example, the display 68 as shown in FIG. 7. A contact condition of little or no contact may be experienced before the electrode 20 of the medical device 16 comes into contact with the target tissue 92. Insufficient contact may inhibit or even prevent adequate lesions from being formed when the medical device 16 is operated to apply ablative energy. A contact condition of light to medium contact may be experienced when, for example, the electrode 20 of the medical device 16 contacts the tissue and slightly depresses the tissue. A contact condition of hard or excessive contact may result in an electrode 20 being depressed deeply into the tissue 92 which may result in the formation of lesions which are too deep and/or the destruction of tissue surrounding the target tissue 92. Accordingly, the user may desire a contact condition of light to medium contact.

It is noted that the exemplary proximity or contact conditions of FIGS. 17A-17C are shown for purposes of illustration and are not intended to be limiting. Other proximity or contact conditions (e.g., finer granularity between contact conditions) may also exist and/or be desired by the user. The definition of such proximity or contact conditions may depend at least to some extent on operating conditions, such as, the type of target tissue, desired depth of the ablation lesion, and operating frequency of the ablation energy, to name only a few examples.

The tissue assessment module 116 of the ECU (see FIG. 7) may monitor electrode impedance changes (e.g., for each electrode) relative to establish baseline impedance values to generate outputs indicative of tissue proximity or contract for each electrode. That is, the tissue assessment module 116 may categorize each electrode as: 1) insufficient electrode coupling; 2) sufficient electrode coupling; and 3) elevated or excessive electrode coupling. One embodiment equates the following change in impedance values relative to a baseline impedance values for the noted conditions:

insufficient electrode coupling: $\Delta Z < 20$ sufficient electrode coupling: $20 < \Delta Z < 200$ elevated/excessive electrode coupling: $\Delta Z > 200$ In such an exemplary embodiment, the contact assessment module 116 may be operatively associated with the processor 96 memory 94 and/or measurement circuit 130 to analyze the change in impedance. By way of example, upon determining a change in an impedance measurement for an electrode, the contact assessment module 116 may determine a corresponding proximity of contact coupling condition for the electrode of the medical device based on the identified change. In an exemplary embodiment, proximity or contact conditions corresponding to changes in impedance values may be predetermined, e.g., during testing for any of a wide range of tissue types and at various frequencies. The proximity or contact conditions may be stored in memory 94, e.g., as tables or other suitable data structures. The processor 96 or contact assessment module 116 may then access the tables in memory 94 and determine a proximity or contact condition corresponding to change in impedance. It is noted that the exemplary proximity or contact ranges shown above are shown for purposes of illustration and are not intended to be limiting. Other values or ranges may also exist and/or be desired by the user. Further, and as is more fully discussed herein, different components of impedance (e.g., resistive component, reactive component and/or phase angle) may be utilized to assess proximity or contact.

Figure 18:
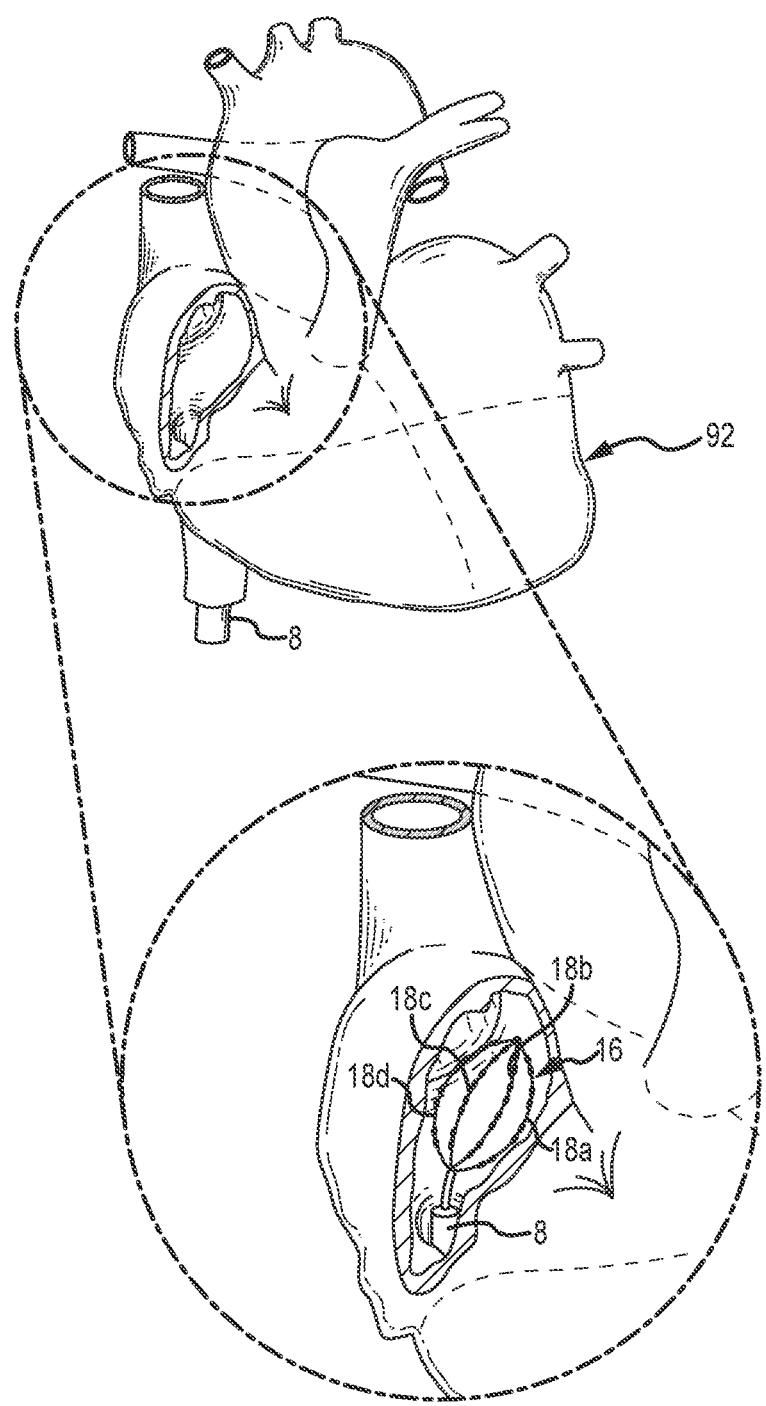
FIG. 18 illustrates a medical device disposed within a heart chamber.

If a baselining or calibration procedure is performed for a medical device or catheter having a single electrode, a limited number of electrodes and/or a single axis configuration (e.g., See FIG. 2), a technician can simply position the electrodes of the device in the blood pool away from tissue, and record the baseline impedances. However, when attempting to acquire baseline impedance information for medical devices having numerous electrodes, large sizes and/or expandable shapes, unique difficulties arise. That is, when measuring impedance on high count electrode catheters and/or on large catheters, it is often impractical to position the catheter in such a way as to avoid tissue contact on all electrodes. By way of example, FIG. 18 illustrates an expandable medical device 16 disposed within the right atrium of a heart 92 of a patient. Initially, the medical device 16 is guided to the right atrium using an introducer 8 routed through an artery of the patient. Once the end of the introducer 8 is positioned proximate to the intersection of the artery and atrium, the expandable basket medical device 16 is disposed through the open end of the introducer 8 and into the atrium. At this time, the shape metal arms 18a-d (hereafter 18 unless specifically referenced) of the medical device 16 expand to the illustrated shape. As discussed above, such a medical device 16 may include multiple electrodes or pairs of electrodes on each arm 18. Due to the size of the medical device 16 and the limited volume of the atrium, it typically is not feasible to maneuver the medical device 16 into a position where all electrodes of the different arms 18 are concurrently disposed within an interior volume of the atrium (e.g., into a blood pool) and free of contact with patient tissue (e.g., atrium wall/surface). That is, if a first arm 18c of the medical device 16 is within the blood pool, an opposing arm 18a will typically be in contact with tissue. Accordingly, a different method for establishing baselines impedance values for each electrode of high electrode count catheters is needed.

Figure 19:
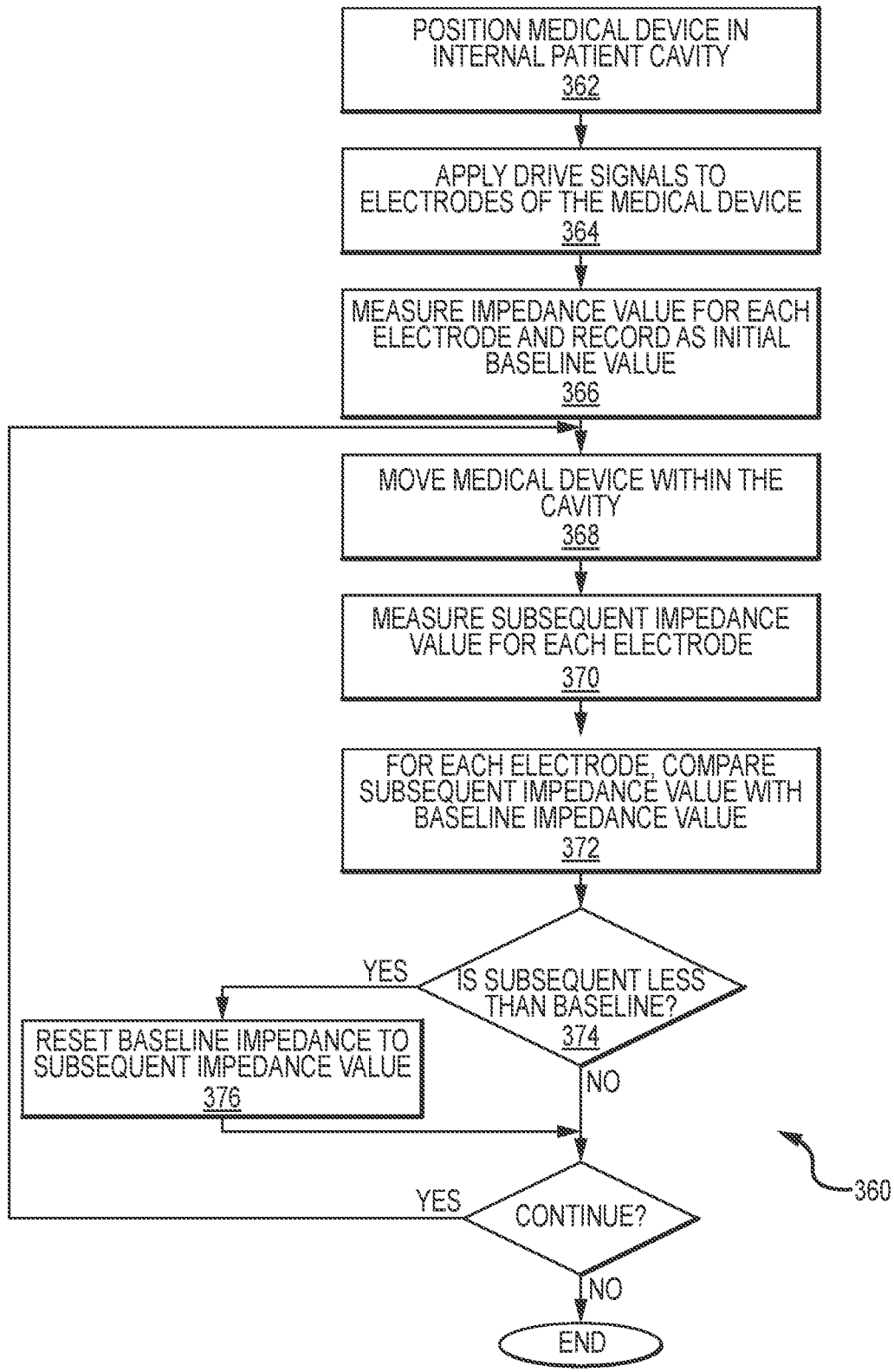
FIG. 19 is a flow chart illustrating a first process for use to determine baseline impedance values.

A first process 360 for establishing baseline impedance values for multiple electrodes of a medical device such as a catheter is illustrated in FIG. 19. Generally, the process entails identifying a minimum impedance value for each electrode over a time period/window and utilizing the identified minimum impedance value as a baseline impedance value for that electrode. Initially, a medical device is positioned 362 within an internal patient cavity (e.g., heart chamber). Once initially positioned, at least a portion of the electrodes of the medical device are expected to be positioned within the interior of the internal patient cavity. For example, at least a portion of the electrodes are positioned within a blood pool of the cavity and free from contact with patient tissue. Once initially positioned, drive signals are applied 364 (e.g., continuously applied) to the electrodes of the medical device. Impedance values are measured for each electrode in response to the drive signals and the impedance values are recorded 366 as initial baseline impedance values for each electrode. Once an initial set of baseline impedance values are recorded, the medical device may be moved 368 within the internal patient cavity in conjunction with application of the drive signals to the electrodes. Such movement may allow a portion of the electrodes to be repositioned such that they are located within the blood pool and away from patient tissue. Conversely, a portion of the electrodes may be positioned from within the blood pool and into contact with patient tissue. Subsequent impedance values (e.g., current impedance values) are measured 370 for each electrode. The subsequent impedance value for each electrode is then compared 372 with the baseline impedance value for that electrode. If the subsequent impedance value is less than the baseline impedance value for an electrode 374, the baseline impedance value is reset 376 to the subsequent impedance value. If the subsequent impedance value is greater than the baseline impedance value, the subsequent impedance value may be discarded. After comparisons are made, the process 360 may continue with additional catheter movement 368 and measurement 370 of subsequent impedance values. In this regard, a series of subsequent impedance values (e.g., time series of impedance values) may be measured for each electrode and each of the series of subsequent impedance values may be compared with previously established baseline value. The process may continue until no subsequent impedance value is less than a previously measured baseline impedance value. Alternatively, the process may continue for a predetermined time (e.g., time window). In the latter regard, such a time window may have a duration during which each electrode would be expected to be disposed within a blood pool for at least one impedance measurement while the medical device is moved about the patient cavity. Once final baseline impedance values are established for the electrodes, subsequent impedance measurements may be compared with the final baseline impedance values to generate indication of tissue proximity or contact.

Figure 20:
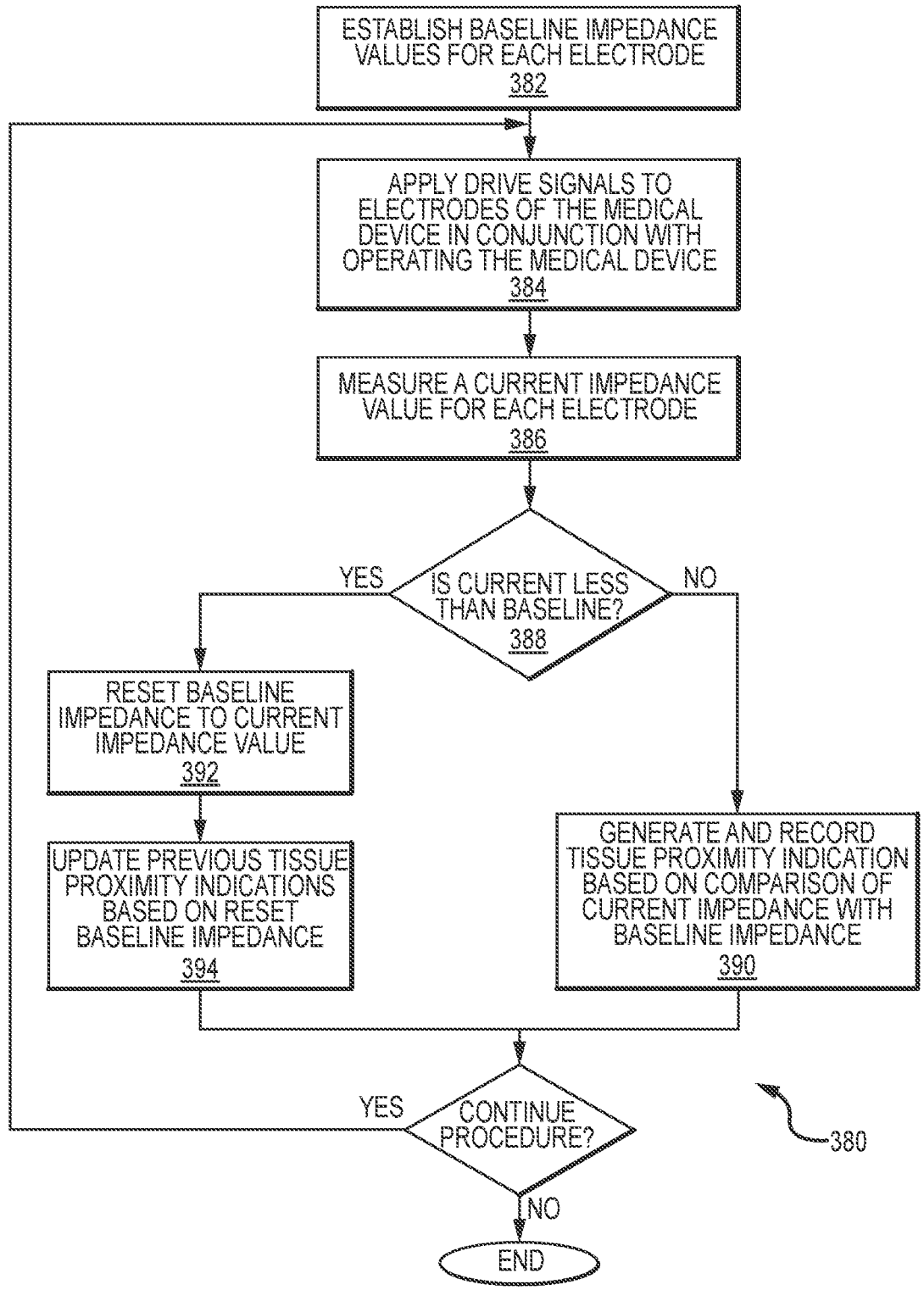
FIG. 20 is a flow chart illustrating a second process for use to determine baseline impedance values.

Another process 380 for establishing baseline impedance values for multiple electrodes of a medical device is illustrated in FIG. 20. Generally, the process entails identifying a minimum impedance value for each electrode during a medical procedure (e.g., ablation procedure) and utilizing the identified minimum impedance value as a baseline impedance value for determining tissue proximity or contact. Initially, a set of baseline impedance values may be established 382 for each electrode. The baseline impedance values may be established as set forth above or these values may be established based on predetermined or default values. During operation of the medical device, drive signals are applied 384 to electrodes of the medical device. In response to the drive signals being applied to the electrodes, an impedance value (e.g., current impedance value) is measured 386 for each electrode. The current impedance values may be stored. A comparison is made between the current impedance value and the baseline impedance value for each electrode to determine 388 if the current impedance value is less than the baseline impedance value. If the current impedance value is greater than the baseline impedance value, a tissue proximity or contact indication is generated 390 based on, for example, a difference in these impedance values. The tissue proximity or contact indication may be stored and/or output to a user. If the current impedance value is less than the baseline impedance value, the baseline impedance value is reset 392 to the current impedance value. That is, a new minimum impedance value for electrode (e.g., current impedance value) replaces a previous baseline impedance value for that electrode. Optionally, previous tissue proximity or contact indications for the electrode may be updated 396 based on the new baseline value. For example, where tissue proximity or contact indications are based on a difference between a baseline impedance value and a current impedance value, resetting of the baseline impedance value to a new lower impedance value may result in changes to previously determined tissue proximity or contact indications. Accordingly, any updates to the previously determined tissue proximity or contact indications may be stored and/or be output to a user. The process may continue for the duration of the procedure.

Figure 21:
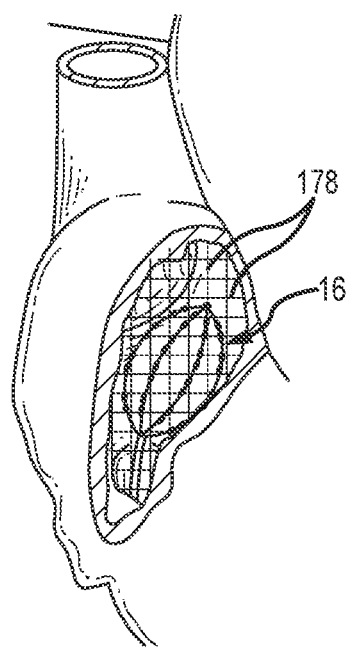
FIG. 21 illustrates dividing an internal patient cavity into sub-regions for baseline impedance determination.

Though discussed above in relation to establishing baseline impedance values (e.g., minimum impedance values) on an electrode-by-electrode basis, the present disclosure provides another process for establishing baseline impedance values. Specifically, a process is provided for establishing spatially-dependent baseline impedance values. Along these lines, baseline impedance values may be established for different regions of an internal patient cavity. FIG. 21 illustrates a medical device 16 as disposed within the right atrium of a patient heart. The interior of the right atrium (e.g., internal patient cavity) is disposed within a three-dimensional space that may be divided into sub-regions as illustrated by the grid 78 shown in FIG. 21. Though shown as a two-dimensional grid for purposes of illustration, it will be appreciated that such a grid 78 may be three dimensional and that the size of its grid cells may be modified. Further, sub-regions (e.g., grid cells) may be otherwise defined (radius-based, region based, designated by an operator, etc.). As noted above, the ECU 72 illustrated in FIG. 7 may be configured to obtain data from various external patch electrodes as well as electrodes of a medical device/catheter to determine the location of the catheter electrodes within a patient (e.g., within the three-dimensional space). As previously discussed, the position of an electrode or multiple electrodes may be determined by driving current between different sets of patches and measuring one or more impedances or other electrical responses. The ability to locate the position of each electrode within a three-dimensional space in conjunction with obtaining impedance values for the electrodes allows for determining impedances at locations (e.g., sub-regions) within the three-dimensional space. Accordingly, the impedances identified for each sub-region within the three-dimensional space may be utilized as baseline impedance values for tissue proximity or contact assessment and/or for lesion formation assessment.

Figure 22:
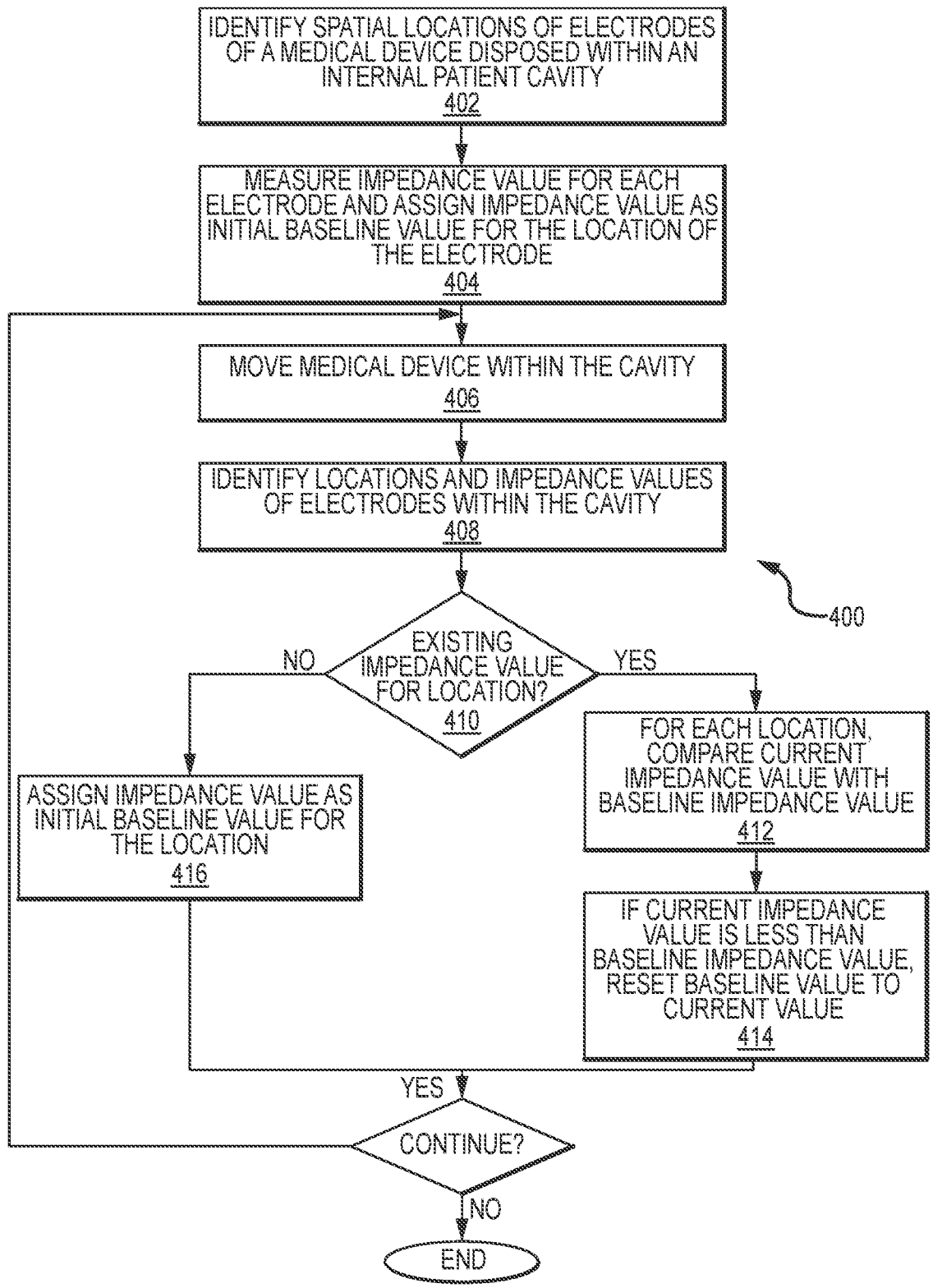
FIG. 22 is a flow chart illustrating a third process for use to determine baseline impedance values.

FIG. 22 illustrates a process 400 for establishing spatially-dependent baseline impedance values. Initially, the process entails identifying 402 spatial locations of electrodes of a medical device disposed within an internal patient cavity (e.g., heart chamber) 402. In conjunction with the identification of the location of the electrodes, the process includes measuring impedance values for each electrode and assigning 404 the impedance values to the location of their corresponding electrode. For instance, each electrode may be identified within one sub-region (e.g., grid cell) of a three-dimensional space and each sub-region including an electrode may be assigned the impedance value of the electrode located therein. Sub-regions that do not include an electrode may be assigned a null value or a default value. The medical device is repositioned or moved 406 within the cavity to relocate the electrodes. In conjunction with such movement, the process further includes identifying 408 updated locations and updated impedance values for the electrodes. That is, the current locations and current impedance values are obtained for the electrodes. Once impedance values are updated, a determination 410 is made based on the location of each of the electrodes. Specifically, it is determined if a baseline impedance values exist for the current locations of the electrodes. For each location having an existing impedance baseline value (e.g., previously assigned baseline impedance value) the current impedance value for that location is compared 412 with the previously assigned baseline impedance value for that location. If the current impedance value is less than the baseline impedance value for that location, the baseline impedance value is reset 414 to the current impedance value. Each location that does not have an existing impedance baseline value is assigned 416 the current impedance value for that location. This process may continue until no current impedance values are less than a previously measured baseline impedance value for any location. Alternatively, the process may continue for a predetermined time (e.g., time window).

The spatially-dependent baseline impedance values may be used for assessing proximity or contact between an electrode and patient tissue. In addition, spatially-dependent baseline impedance values may provide an improved means for assessing lesion formation in tissue. That is, during a procedure where baseline impedance values are assessed for sub-regions that correspond to tissue surfaces (e.g., wall of the internal patient cavity), changes in subsequent impedance values correspond with changes in the tissue itself. Thus, these changes provide an indication of lesion formation.

Figure 23B:
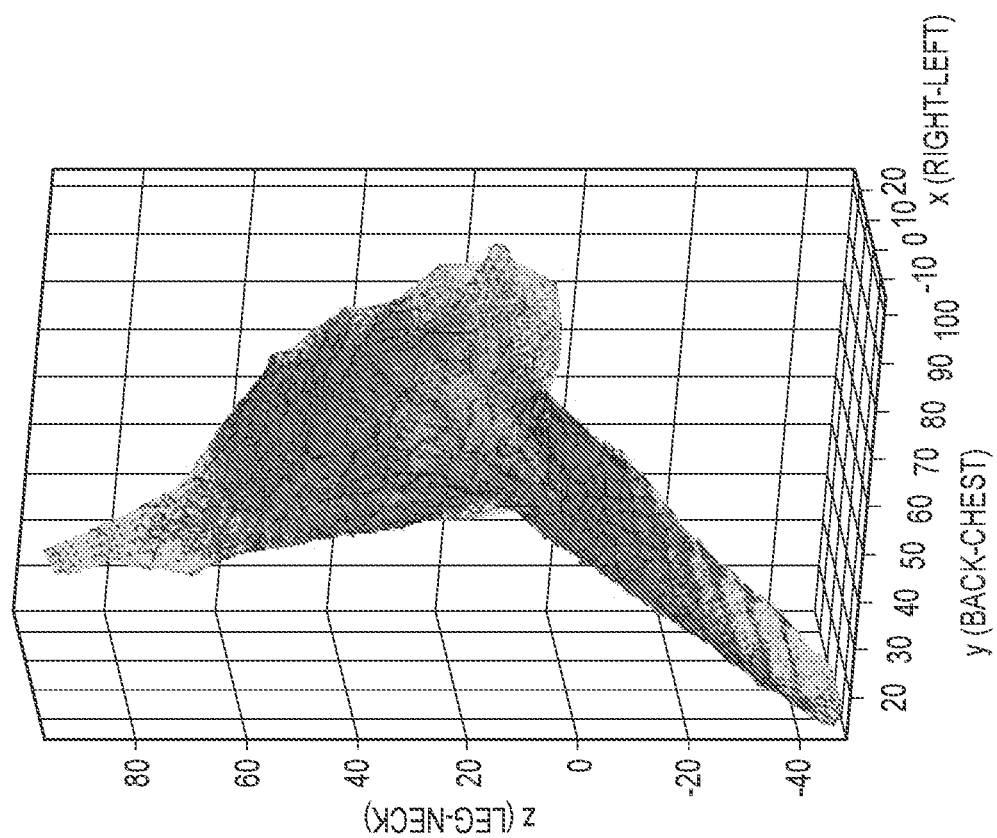
FIGS. 23A and 23B illustrate contact maps showing a geometry of an internal patient cavity.
Figure 23A:
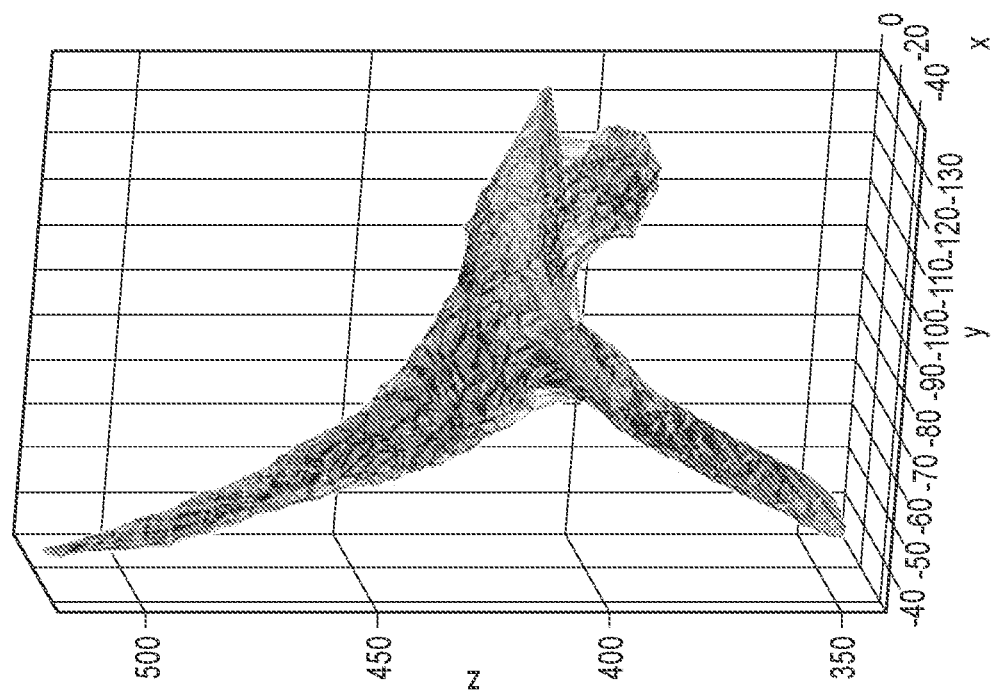

After or in conjunction with establishing baseline impedance values, subsequent impedance measurements may be compared to the to the baseline impedance values to generate an indication of tissue proximity or contact. This may be done in various ways. In the simplest form, a change between a subsequent impedance value and a baseline impedance value, greater than predetermined threshold value (which may be set heuristically or empirically), indicates tissue contact. That is, when the impedance change is greater that the threshold value, tissue contact is considered to exist between an electrode and the tissue. Such a simplified tissue contact assessment may be sufficient when a binary indication of tissue contact is all that is required. For instance, such binary tissue contact may be utilized to map the interior of a patient cavity. Such a binary contact assessment for mapping is shown in FIGS. 23A and 23B, which illustrate surfaces (e.g., voltage maps) generated based on contacts between electrodes and patient tissue within an internal patient cavity. As shown, the maps plot identified locations on a display that correspond to physical locations of the electrodes within the patient. FIG. 23A illustrates a display output generated by a medical device utilized to map the right atrium of a patient heart. During such a procedure, after establishing baseline impedance values or in conjunction with establishing baseline impedance values, the medical device is moved around the atrium to map its interior space. Each time an electrode contacts tissue and a resulting change of the measured impedance differs from a baseline impedance for that electrode by more than the threshold amount, a location of the contacting electrode is recorded and output on the display. Over time, a surface geometry for the interior of the cavity (e.g., atrium) may be generated. FIG. 23B illustrates mapping of the same space where a threshold for binary contact assessment is reduced. As shown, by reducing the threshold, more contact points may be identified resulting in a more complete map of the interior of the patient cavity. As all of the impedance values are stored, a user may perform a mapping procedure and then adjust the thresholds to correspondingly the contact points shown on the map. Further, maps having different thresholds may be combined to generate composite maps.

In other applications, multiple thresholds may be utilized. Such multiple thresholds may allow generating indicators associated with various levels of tissue contact. For example, instead of using binary thresholds, the impedance values may be utilized as indicators of tissue contact confidence. For instance, ranges of contact indications (e.g., insufficient, sufficient, elevated, etc.) may be generated as set forth above. When output to a display, such indication could, for example, be used to color geometry surfaces, scale voltage maps, and/or assist with lesion prediction.

Figure 24:
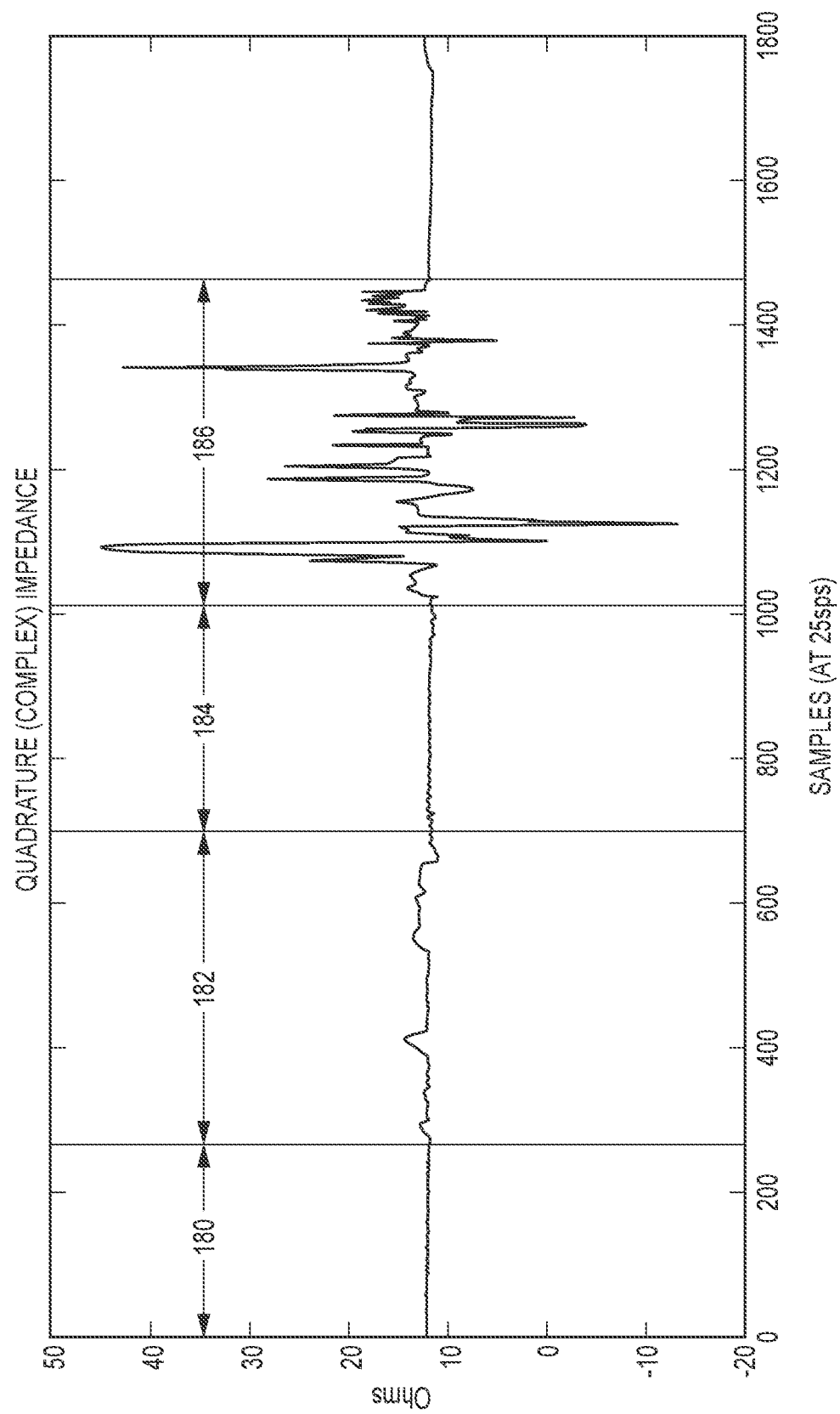
FIG. 24 illustrates a quadrature impedance response of an electrode for different contacts.

In addition to utilizing the measured impedance values to assess tissue proximity or contact, it will be noted that different components of the impedance values may be utilized for such assessments. That is, the systems and processes discussed above measure both resistive (real) and reactive (quadrature) impedance. When assessing tissue contact, the correlation between these two components is very high, with the resistive component changing the most. That is, the phase of the impedance is constant, and changes to the phase are minimal. The quadrature component (and phase), however, changes significantly when an electrode enters and exits an introducer (i.e., is sheathed or unsheathed) and when an electrode that comes in contact with another electrode. This is illustrated in FIG. 24, which shows the quadrature impedance response of one electrode prior to tissue contact 180, during tissue contact 182, after tissue contact 184, and during sheathing or contact with another electrode 186 (or other anomalous event). As shown, the change in the quadrature component is minimal before, during and after tissue contact. In contrast, when the electrode is sheathed or contacts another electrode, the quadrature response of the electrode spikes. Accordingly, in one embodiment, it may be sufficient to utilize the resistive component of impedance (e.g., real component) for tissue contact assessment and to utilize the quadrature component of impedance to differentiate between an increase of impedance due to tissue contact versus an increase of impedance due to sheathing and/or contacting other electrodes. This may serve an important purpose if a medical device is being used autonomously during a procedure to assess and/or exclude other data. In the latter regard, increases of the quadrature component of the impedance above a predetermined threshold may indicate sheathing and/or contact with other electrode(s) and any impedance measurement (e.g., resistive measurements) obtained during this time may be discarded. That is, the impedance measurements may be invalidated due to sheathing or electrode contact interference. Alternatively, the magnitude/amplitude of any drive signals and/or any ablation energy applied to applied to any electrode identified as having an increased quadrature component of impedance may be altered (e.g., reduced).

In an embodiment, the magnitude of the quadrature component may be utilized to identify when an electrode enters or exits a sheath. As illustrated in FIG. 24, spikes in the quadrature component (e.g., section 186) may indicate a number of anomalous events including contact with another electrode, an electrode entering or exiting an introducer and/or the failure of a path electrode (e.g., see FIG. 7). By way of example only, different events may be associated with different thresholds. Referring again to FIG. 24, it is noted that the magnitude of the quadrature component is set forth in Ohms. The magnitude of a deviation of the magnitude of the quadrature component may be correlated to different event, for example, empirically. Small deviations (e.g., 10-15 Ohms) may represent contact with other electrodes. Larger magnitude deviations (e.g., 20-50 Ohms) may be identified as entry or exit of an electrode into or from an introduce. High magnitude deviations (e.g., 200+ Ohms) may be identified as patch failure (e.g., a body patch disconnect). It will be appreciated that the ranges discussed are exemplary and other ranges may be established and/or correlated to other events.

Figure 25:
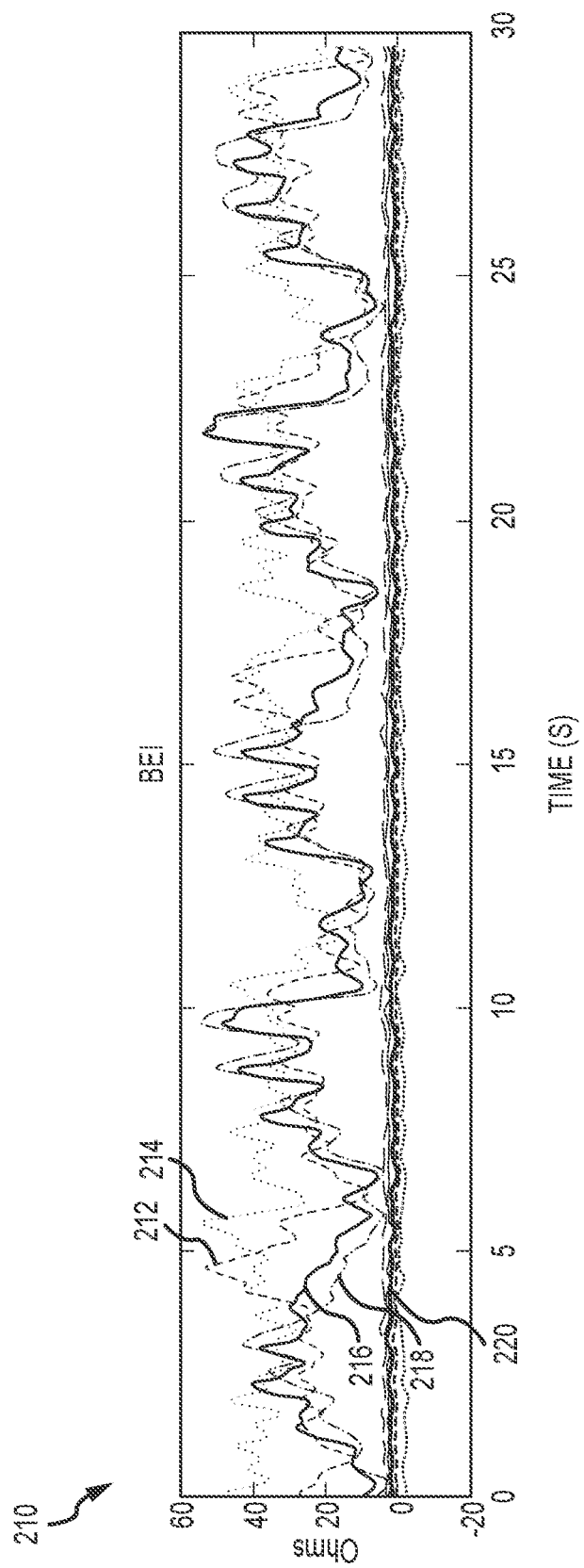
FIG. 25 is first graph of impedance responses of electrodes over time.
Figure 26:
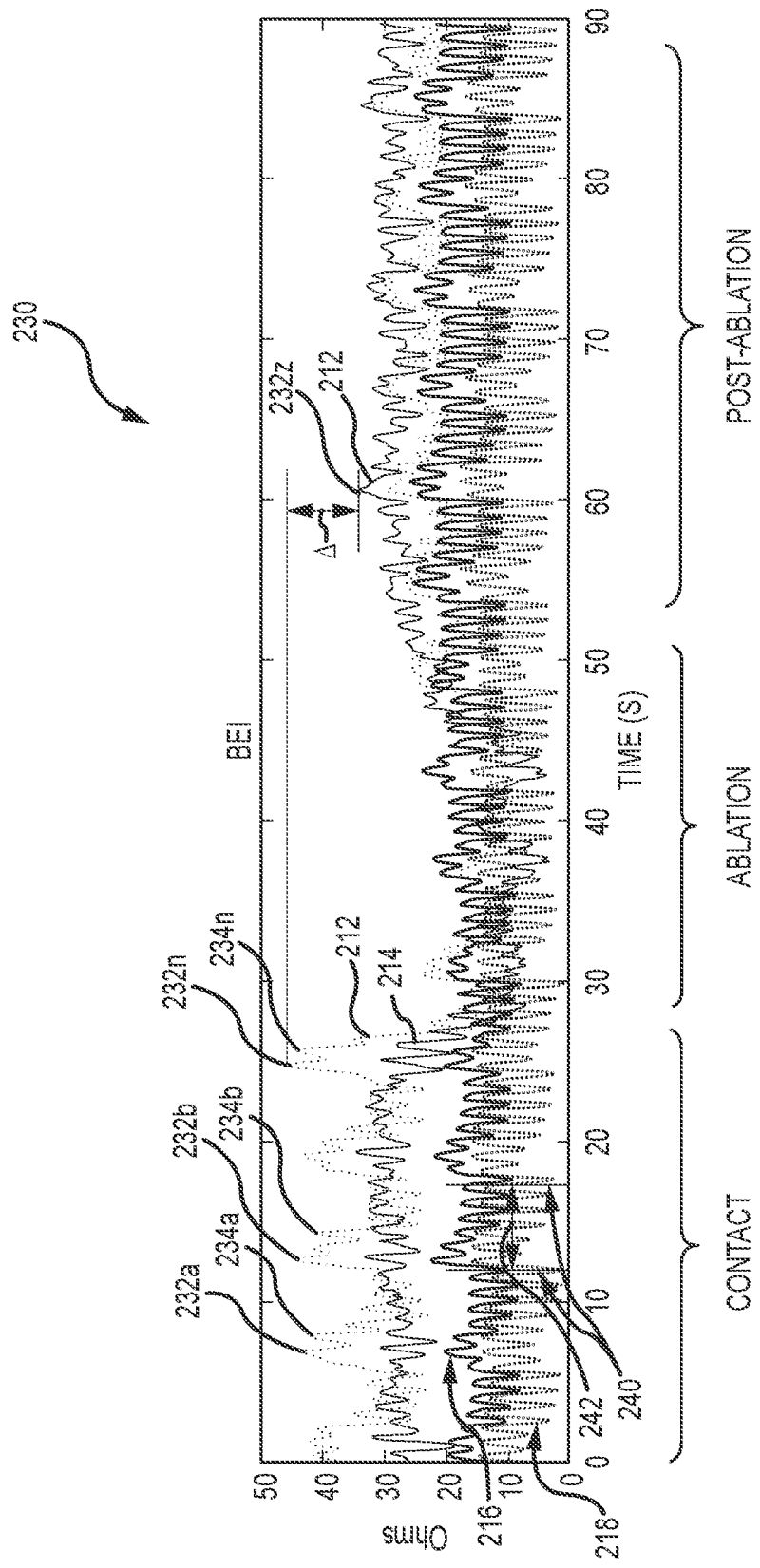
FIG. 26 is a second graph of impedance responses of electrodes over time.

While contact assessment and/or lesion assessment is facilitated using the above-noted systems and processes, it recognized that electrode impedance measurements are often not a stable quantity due to patient respiration and/or cardiac motion of the heart. Along these lines, there are instances that an electrode may be in a blood pool but come into periodic contact with tissue due to generally period respiration and/or cardiac motion. FIGS. 25 and 26 illustrates two graphs 210 and 230 that illustrate the impedance response of a plurality of electrodes over time. More specifically, FIG. 25 illustrates the response of a medical device similar to the device shown in FIG. 17C where the device has four arms (e.g., splines) and each arm has four electrodes. In the response graph 210 illustrated in FIG. 25, a single arm of the medical device and its four electrodes are in contact with patient tissue while the remaining electrodes (e.g., attached to other arms) are out of contact with the patient tissue. As shown, the magnitude of the responses 212, 214, 216 and 218 (shown in Ohms) of the four contacting electrodes vary over time while the responses (collectively 220) of the non-contacting electrodes remain substantially constant over time. The variation of the responses 212-218 for the contacting electrode are better illustrated in FIG. 26, which illustrates these responses before, during and after ablation.

Referring to response 212 in FIG. 26, it is noted that the response 212 has periodic major peak magnitudes 232a-232n that correspond with respiration of the patient. The response 212 also has minor peak magnitudes 234a-234n that correspond with cardiac motion. When contact exists and is maintained between electrodes and tissue, it is observable that respiration and/or cardiac motion often (but not always) modulates the level of contact (e.g., impedance magnitude). Along these lines, a contact assessment scheme utilizing a single contact threshold may intermittently trigger back and forth due to respiration and/or cardiac motion. This may be perfectly acceptable, as it accurately portrays a modulating level of contact. However, it may also be a nuisance for a user as the contact levels continually fluctuate. To counteract such continual fluctuation, contact assessment measurements may be time averaged or obtained during common times during a respiratory or cardiac cycle. In the former regard, impedance measurements may be acquired and averaged over a time window that corresponds with, for example, a single heartbeat or respiration cycle. Such a time window 240 is illustrated in conjunction with response 218 where the horizontal line represents an average impedance 242 over the time window 240. In the latter regard, impedance measurements may be taken at common points or phases (e.g., peak or trough points) of a respiration or cardiac cycle. That is, impedance measurements may be correlated with respiratory and/or cardiac motion. In such instances, the system (e.g., ECU) may obtain respiratory or cardiac motion information from one or more sensors (e.g., EGC lead 90; see FIG. 7). Such a time windowing approach or correlation approach may improve the stability of contact assessment outputs. However, this may result in a modest delay between contact updates. Further, the time windowing approach and correlation approach may each be utilized in establishing baseline impedance values.

FIG. 26 further illustrates impedance monitoring throughout a medical procedure. Specifically, FIG. 26 illustrates continual impedance monitoring of four electrodes in contact with patient tissue before, during and after application of ablation energy to the tissue. As shown, the responses 212-218 change between pre-ablation contact and during ablation. In the illustrated graph 230, the impedance responses 212-218 have a reduced magnitude during ablation compared to pre-ablation. Further, the magnitude of the responses 212-218 tend to slightly increase post-ablation. However, it is noted that the post-ablation magnitudes of the impedance responses do not return to pre-ablation magnitudes. Referring to impedance response 212, it is noted that a peak magnitude 232$n$ of impedance response 212 prior to ablation is greater than a peak magnitude 232$z$ after ablation. This difference $\Delta$ provides an indication of lesion formation in the tissue. Accordingly, such a difference may be utilized by the processor or contact assessment module to generate an output indicative of lesion formation in tissue. Further, this indication of lesion formation may be incorporated onto or into, for example, the maps shown in FIGS. 23A and 23B. That is, the location of an electrode and the change in impedance before and after ablation may be plotted onto a map. Along these lines, the ability to establish spatially-dependent baseline impedance values as discussed in relation to FIG. 22 provides a mechanism for readily recording impedance changes on a surface of the patient tissue in the event that the electrodes move during an ablation procedure. For instance, if an ablation electrode is drawn over tissue during application of ablation energy to create a linear lesion, the location of the electrode providing an impedance measurement for a tissue location may change. However, when utilizing medical devices having high numbers of electrodes (e.g., 100 or 200), it is expected that another electrode will measure the response of the tissue location such that pre-ablation and post-ablation impedances may be compared for the tissue location.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

Although numerous embodiments have been described above with a certain degree of particularity, those skilled in the art could make numerous alterations to the disclosed embodiments without departing from the spirit or scope of this disclosure. For instance, the present disclosure discusses a bi-pole configuration where each pair of electrodes is independent of all other pairs of electrodes. However, another possibility is to configure electrodes such that one side of each bi-pole is a common electrode. For example, with reference to the catheter of FIG. 2, the tip electrode 22 may form a common electrode for each of the additional ring electrodes 20A-I. That is, tip electrode 22 may be one electrode of each pair of electrodes.

All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the any aspect of the disclosure. As used herein, the phrased "configured to," "configured for," and similar phrases indicate that the subject device, apparatus, or system is designed and/or constructed (e.g., through appropriate hardware, software, and/or components) to fulfill one or more specific object purposes, not that the subject device, apparatus, or system is merely capable of performing the object purpose. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for use with a medical device configured for insertion within a patient, comprising:

applying a plurality of drive signals, each drive signal having a unique frequency that is a harmonic of a common base frequency, across different pairs of electrodes of a medical device having a plurality of electrodes;

measuring a series of subsequent impedance values for each of the plurality of electrodes of the medical device in response to the applying of the plurality of drive signals; and for each electrode:

comparing each subsequent impedance value of the series of subsequent impedance values to a baseline impedance value for the electrode;

generating an indication of tissue proximity of the electrode relative to tissue if the subsequent impedance value is greater than the baseline impedance value; and displaying the indication of tissue proximity of the electrode relative to the tissue on a display.

2. The method of claim 1, further comprising:

resetting the baseline impedance value to the impedance value if the subsequent impedance value is less than the baseline impedance value.

3. The method of claim 1, wherein measuring the series of subsequent impedance values further comprises:

synchronously demodulating responses of the plurality of electrodes to the simultaneously applied drive signals for each of the unique frequencies.

4. The method of claim 1, wherein the measuring of the series of subsequent impedance values for each of the plurality of electrodes further comprises:

measuring the subsequent impedance value for each of the plurality of electrodes during movement of the medical device, wherein positions of at least a portion of the plurality of electrodes changes.

5. The method of claim 1, wherein the indication of tissue proximity comprises one of:

a binary indication of contact or non-contact between the electrode and the tissue; and a range of contact conditions indicative of a level of contact between the electrode and the tissue.

6. The method of claim 1, wherein the impedance values comprise complex impedance values having a real component and a quadrature component.

7. The method of claim 6, wherein the comparing and the generating further comprise:

comparing the real component of the impedance value to a real component of the baseline impedance value; and generating the indication of tissue proximity based on the comparison of the real component of the impedance value and a real component of the baseline impedance value.

8. The method of claim 6, further comprising:

comparing the quadrature component of the impedance value to a quadrature component of the baseline impedance value; and upon the quadrature component of the impedance value exceeding the quadrature component of the baseline impedance value by a predetermined threshold, generating an output.

9. The method of claim 6, wherein generating the output comprises generating at least one of:

an indication that an electrode has entered or exited an introducer; and an indication that a patch electrode used in the applying of the plurality of drive signals is malfunctioning.

10. The method of claim 1, further comprising, for each electrode:

identifying a location of the electrode relative to an internal patient cavity, wherein the indication of tissue proximity is displayed on the display at a corresponding location on a map of the internal patient cavity.

11. The method of claim 1, further comprising:

receiving an input indicative of motion of the tissue caused by at least one of respiration and cardiac motion, wherein the indication of tissue proximity is altered based on the indication of motion.

12. The method of claim 11, wherein the current impedance values are generated in correlation with a phase of the motion.

13. A non-transitory computer readable medium storing computer executable instructions, executable by a processor to:

apply a plurality of drive signals, each drive signal having a unique frequency that is a harmonic of a common base frequency, across different pairs of electrodes of a medical device having a plurality of electrodes;

measure a series of subsequent impedance values for each of the plurality of electrodes of the medical device in response to the applying of the plurality of drive signals; and for each electrode:

compare each subsequent impedance value of the series of subsequent impedance values to a baseline impedance value for the electrode;

generate an indication of tissue proximity of the electrode relative to tissue if the subsequent impedance value is greater than the baseline impedance value; and display the indication of tissue proximity of the electrode relative to the tissue on a display.

14. The non-transitory computer readable medium of claim 13, further comprising instructions executable by the processor to:

reset the baseline impedance value to the impedance value if the subsequent impedance value is less than the baseline impedance value.

15. The non-transitory computer readable medium of claim 13, further comprising instructions executable by the processor to:

measure the subsequent impedance value for each of the plurality of electrodes during movement of the medical device, wherein positions of at least a portion of the plurality of electrodes changes.

16. The non-transitory computer readable medium of claim 13, further comprising instructions executable by the processor to generate at least one of:
   a binary indication of contact or non-contact between the electrode and the tissue; and
   a range of contact conditions indicative of a level of contact between the electrode and the tissue.

17. The non-transitory computer readable medium of claim 13, wherein the impedance values comprise complex impedance values having a real component and a quadrature component.

18. The non-transitory computer readable medium of claim 17, further comprising instructions executable by the processor to:
   compare the real component of the impedance value to a real component of the baseline impedance value; and
   generate the indication of tissue proximity based on the comparison of the real component of the impedance value and a real component of the baseline impedance value.

19. The non-transitory computer readable medium of claim 17, wherein the step of generating the output comprises generating at least one of:
   an indication that an electrode has entered or exited an introducer; and
   an indication that a patch electrode used in the applying of the plurality of drive signals is malfunctioning.

20. The non-transitory computer readable medium of claim 13, further comprising instructions executable by the processor to:
   identify a location of the electrode relative to an internal patient cavity, wherein the indication of tissue proximity is displayed on the display at a corresponding location on a map of the internal patient cavity.

* * * * *